(12) United States Patent
Fan et al.

(10) Patent No.: US 12,398,374 B2
(45) Date of Patent: Aug. 26, 2025

(54) METHOD FOR PREPARING INDUCED PLURIPOTENT STEM CELLS BY REPROGRAMMING SOMATIC CELLS

(71) Applicant: ZHEJIANG HUODE BIOENGINEERING COMPANY LIMITED, Hangzhou (CN)

(72) Inventors: Jing Fan, Hangzhou (CN); Fang Ren, Hangzhou (CN); Anxin Wang, Hangzhou (CN)

(73) Assignee: ZHEJIANG HUODE BIOENGINEERING COMPANY LIMITED, Zhejiang (CN)

( * ) Notice: Subject to any disclaimer, the term of this patent is extended or adjusted under 35 U.S.C. 154(b) by 811 days.

(21) Appl. No.: 17/597,970

(22) PCT Filed: Jul. 31, 2020

(86) PCT No.: PCT/CN2020/106327
§ 371 (c)(1),
(2) Date: Jan. 31, 2022

(87) PCT Pub. No.: WO2021/018296
PCT Pub. Date: Feb. 4, 2021

(65) Prior Publication Data
US 2022/0325248 A1   Oct. 13, 2022

(30) Foreign Application Priority Data
Aug. 1, 2019 (CN) .......................... 201910707125.0

(51) Int. Cl.
| | |
|---|---|
| *C12N 5/074* | (2010.01) |
| *C07K 14/47* | (2006.01) |
| *C07K 14/71* | (2006.01) |
| *C12N 5/10* | (2006.01) |
| *C12N 9/12* | (2006.01) |
| *C12N 15/85* | (2006.01) |
| *C12N 15/86* | (2006.01) |

(52) U.S. Cl.
CPC ........ *C12N 5/0696* (2013.01); *C07K 14/4705* (2013.01); *C12N 5/10* (2013.01); *C12N 15/85* (2013.01); *C12N 15/86* (2013.01); *C07K 14/71* (2013.01); *C12N 9/1205* (2013.01); *C12N 2501/01* (2013.01); *C12N 2501/15* (2013.01); *C12N 2501/603* (2013.01); *C12N 2501/605* (2013.01); *C12N 2501/727* (2013.01); *C12N 2506/11* (2013.01); *C12N 2506/1307* (2013.01); *C12N 2510/00* (2013.01); *C12N 2760/18843* (2013.01); *C12N 2820/60* (2013.01)

(58) Field of Classification Search
CPC ........ C12N 5/0696; C12N 5/10; C12N 15/85; C12N 2501/01; C12N 2501/603; C12N 2501/605; C12N 2510/00; C12N 2760/18843; C12N 2820/60; C12N 9/1205; C12N 2501/15; C12N 2501/415; C12N 2501/727; C12N 2506/11; C12N 2506/1307; C12N 2533/52; C12N 2533/90; C12N 15/86; C07K 14/4705; C07K 14/71
USPC ....... 435/456, 461, 325, 357, 366, 372, 377; 530/358; 536/23.1
See application file for complete search history.

(56) References Cited

U.S. PATENT DOCUMENTS

| | | |
|---|---|---|
| 10,231,999 B2 | 3/2019 | Lee et al. |
| 2019/0024047 A1 | 1/2019 | Matsumoto et al. |

FOREIGN PATENT DOCUMENTS

| | | | |
|---|---|---|---|
| CN | 104673741 A | * | 6/2015 |
| CN | 109679921 A | | 4/2019 |
| EP | 3272858 A1 | | 1/2018 |
| WO | WO 2009/117439 A2 | | 9/2009 |
| WO | WO 2012/087965 A2 | | 6/2012 |
| WO | WO 2015/003643 A1 | | 1/2015 |

OTHER PUBLICATIONS

Li et al. 2017, Cell Stem Cell, vol. 21, 264-273. (Year: 2017).*
Chichagova et al. 2015, Method in Molecular Biology, vol. 1353, 285-307. (Year: 2015).*
Storm et al. 2007, Journal of Biological Chemistry, vol. 282(9), 6265-6273. (Year: 2007).*
Zhao et al. 2018, Journal of Experimental Zoology Part B: Molecular and Developmental Evolution, vol. 330(8), 406-416. (Year: 2018).*
Zhou & Sun 2019, Current Molecular Medicine, vol. 19, 77-90. (Year: 2019).*
Chinese Search Report for Chinese Patent Application No. 2020800064401, dated Aug. 18, 2022, 2 pages.
Extended European Search Report for Application No. 20847071.6, dated Sep. 15, 2022, 10 pages.
(Continued)

*Primary Examiner* — Maria G Leavitt
*Assistant Examiner* — Katie L Pennington
(74) *Attorney, Agent, or Firm* — Sughrue Mion, PLLC

(57) ABSTRACT

The present invention provides a method for preparing induced pluripotent stem cells through somatic cell reprogramming and induced pluripotent stem cells obtained therefrom. The present method comprises introducing the factors Oct4 and Nanog as reprogramming-inducing factors into somatic cells to perform reprogramming; followed by culturing the partially or fully reprogrammed somatic cells in a medium comprising specific chemical inducing agents to obtain induced pluripotent stem cells. In the present invention, the combination of different forms of reprogramming-inducing factors and three small-molecule compounds as chemical inducing agents can significantly improve the reprogramming efficiency of human somatic cells and reduce the tumorigenicity of the obtained induced pluripotent stem cells.

15 Claims, 6 Drawing Sheets
Specification includes a Sequence Listing.

(56) References Cited

OTHER PUBLICATIONS

Ichida et al., "A-Small-Molecule Inhibitor of Tgf-beta Signaling Replaces Sox2 in Reprogramming by Inducing Nanog," Cell Stem Cell, 2009, 5:491-503,.

Lewandowski et al., "Techniques of Human Embryonic Stem Cell and Induced Pluripotent Stem Cell Derivation," Arch Immunol Ther Exp, 2016, 64:349-370.

Li et al., "Generation of Human-Induced Pluripotent Stem Cells in the Absence of Exogenous Sox2," Stem Cells 2009, 27:2992-3000.

Li et al., "Generation of iPSCs from mouse fibroblasts with a single gene, Oct4, and small molecules," Cell Res, 2011, 21:196-204.

Xie et al., "Pharmacological Reprogramming of Somatic Cells for Regenerative Medicine," Acc Chem Res, 2017, 50:1202-1211.

Zhou et al., "Research Progress on Somatic Cell Reprogramming Mechanism," Chin J Cell Biol, 2019, 41(5): 805-821.

Extended European Search Report dated Sep. 30, 2024 from the European Patent Office in Application No. 21896169.6.

Adelya A Galiakberova et al., "Neural Stem Cells and Methods for Their Generation From Induced Pluripotent Stem Cells in vitro", Frontiers in Cell and Developmental Biology, Oct. 2020, vol. 8, Article 815, pp. 1-20 (20 pages total).

Jeong Su Byun et al., "Rapid differentiation of astrocytes from human embryonic stem cells", Neuroscience Letters, 2020, vol. 716, No. 134681, pp. 1-7 (7 pages total).

Jin-Chong Xu et al., "Cultured networks of excitatory projection neurons and inhibitory interneurons for studying human cortical neurotoxicity", Neurotoxicity, 2016, vol. 8, Issue 333, pp. 1-14 (14 pages total).

Su-Chun Zhang et al., "In vitro differentiation of transplantable neural precursors from human embryonic stems cells", nature biotechnology, 2001, vol. 19, pp. 1129-1133 (5 pages total).

\* cited by examiner

METHOD FOR PREPARING INDUCED PLURIPOTENT STEM CELLS BY REPROGRAMMING SOMATIC CELLS

This application is a national stage filing under 35 U.S.C. § 371 of International Application No. PCT/CN2020/106327, filed on Jul. 31, 2020, which claims priority of Chinese Application No. 201910707125.0, filed on Aug. 1, 2019. The contents of each of these applications are incorporated herein by reference.

TECHNICAL FIELD

The present disclosure belongs to the technical field of stem cells, and particularly relates to a method of preparing induced pluripotent stem cells through somatic cell reprogramming, as well as the induced pluripotent stem cells obtained therefrom.

BACKGROUND

In 2006, Yamanaka's team developed a cocktail consisting of four genes, namely Oct4, Sox2, Klf4 and c-Myc, which was used to successfully reprogram terminally differentiated skin fibroblasts into induced pluripotent stem cells (iPSCs) by viral infection. One year later, James Thomson successfully reprogrammed human fibroblasts into iPSCs by episomal plasmid transfection using a different combination of four factors (Oct4, Sox2, Nanog and Lin28). The above methods, which are relatively simple and stable in technology, break through the ethical limitations of using human embryonic stem cells in medicine, capable of solving the problem of immune rejection in cell transplantation therapy, and greatly expand the application potential of stem cell technology in clinical medicine. In addition, iPSCs technology and functional cells obtained by subsequent differentiation have great potential value in areas such as cell replacement therapy, pathogenesis research, and new drug screening.

However, with the development of iPSCs reprogramming technology, the drawbacks and problems of iPSCs reprogramming by exogenous introduction of transcription factors have gradually become prominent, such as incomplete reprogramming of some cells, low reprogramming efficiency, and oncogenicity of the introduced proto-oncogenes. Therefore, researchers are trying to find alternatives to the four factors and to optimize the reprogramming system, such as replacing oncogenic transcription factors, adding transcription factors or compounds that enhance reprogramming efficiency, or even completely giving up transcription factors and switching to small molecule compounds to induce somatic cell reprogramming, so as to avoid the potential defects to a certain extent.

At present, a variety of small molecule compounds have been found to induce the generation of pluripotent stem cells. Some of these small molecules directly improve the reprogramming efficiency of recipient cells by inhibiting genomic methylation; some of them affect specific signaling pathways, rendering the intermediate transitional cells and partially reprogrammed cells generated during the reprogramming process to be transformed into stably and completely induced pluripotent stem cells. For example, TGFβ can induce the expression of EMT-related gene SNAIL in the early stage of reprogramming, thereby inducing EMT and hindering the reprogramming process; on the contrary, TGFβ receptor inhibitors can improve the reprogramming efficiency and can be used to replace Sox2 and c-Myc in Yamanaka four factors; cyclic AMP (cAMP) agonists can increase Oct4 expression; glycogen synthase kinase (GSK) inhibitors can increase Nanog expression, thereby improving the reprogramming efficiency of specific cells. Some methods even use a cocktail of purely chemical small molecules without involving any exogenously introduced transcription factors. However, such methods have relatively low reprogramming efficiency and are time-consuming, which cannot meet clinical needs. Some of the methods have not been used for the reprogramming of human cells.

To date, researchers have tried reprogramming techniques on many different types of cells and have achieved success. iPSCs can be obtained by reprogramming using genes, RNAs or proteins of the four factors.

Collectively the characteristics of the above methods, it is important and meaningful to provide a preparation method of adding a combination of reprogramming-inducing factors in different types of vectors and small molecule compounds, so as to improve the reprogramming efficiency, and to obtain iPSCs by safely and effectively reprogramming human somatic cells.

SUMMARY OF THE INVENTION

One purpose of the present invention is to provide a method of preparing induced pluripotent stem cells (iPSCs) by reprogramming of somatic cells.

Another purpose of the present invention is to provide induced pluripotent stem cells (iPSCs) prepared by the method as above.

The present inventors found that by introducing only two transcription factors as reprogramming-inducing factors, accompanied with three small molecule compounds as chemical inducing agents, a simpler and more efficient reprogramming method with broader application potentials as compared to the prior art can be achieved on somatic cells from different origins of the human body, and iPSCs were successfully obtained therefrom, thus completing the present invention.

Accordingly, in a first aspect, the present invention provides a method for preparing induced pluripotent stem cells through somatic cell reprogramming, comprising the following steps: (1) introducing Oct4 and Nanog as reprogramming-inducing factors into somatic cells to preform reprogramming; (2) culturing partially or completely reprogrammed somatic cells obtained in step (1) in the presence of chemical inducing agents to obtain induced pluripotent stem cells (iPSCs), wherein the chemical inducing agents comprise a TGFβ receptor inhibitor, a cyclic AMP (cAMP) agonist and a glycogen synthase kinase (GSK) inhibitor.

Preferably, the TGFβ receptor inhibitor is 616452, and/or the cyclic AMP (cAMP) agonist is Forskolin, and/or the glycogen synthase kinase (GSK) inhibitor is TD114-2.

In the method of the present invention, preferably, Oct4 and Nanog as the reprogramming-inducing factors can be introduced into somatic cells in the form of their DNAs, in the form of their RNAs, or in the form of their protein products. In the method of the present invention, preferably, the somatic cells can be any cells known in the art, for example, skin-derived cells, blood-derived cells, and can also include urine-derived cells, liver cells, epithelial cells, gastric cells, keratinocytes and the like. In a more preferred embodiment, the skin-derived cells may be skin fibroblasts. In another more preferred embodiment, the blood-derived cells may be erythroid progenitor cells.

In the method of the present invention, preferably, the somatic cells are derived from human, that is, human somatic cells.

In the method of the present invention, preferably, the working concentration of the TGFβ receptor inhibitor such as 616452 is 0.1-20 μM, more preferably 5-10 μM, and still more preferably 5 μM.

In the method of the present invention, preferably, the working concentration of the cyclic AMP (cAMP) agonist such as Forskolin is 0.1-50 μM, more preferably 2-20 μM, and still more preferably 10 μM.

In the method of the present invention, preferably, the working concentration of the glycogen synthase kinase (GSK) inhibitor such as TD114-2 is 0.1-20 μM, more preferably 2-10 μM, still more preferably 5 μM.

In a specific embodiment, in step (1), reprogramming is conducted by transfecting the vector(s) comprising the coding sequences of the reprogramming-inducing factors Oct4 and Nanog, respectively, into somatic cells by electroporation or chemical transfection. For example, the transfection can be performed by electroporation. Specifically, the electroporation method may include adding reprogramming vector(s) comprising the inducing factors Oct4 and Nanog to cell suspension, transferring into electroporation cuvette after mixing, placing the electroporation cuvette in the electroporation apparatus, and performing electroporation.

In another specific embodiment, in step (1), reprogramming is conducted by infecting the somatic cells with a virus comprising Oct4 and Nanog reprogramming-inducing factors. Preferably, the virus is Sendai Virus.

In the method of the present invention, preferably, the aforesaid specific chemical inducing agents are added to the culture medium from Day 2 after the introduction of the reprogramming-inducing factors.

In a second aspect, the present invention provides an induced pluripotent stem cell which is obtained by the method of the first aspect.

In a third aspect, the present invention relates to a combination of exogenously introduced two inducing factors and three chemical inducing agents, for use in reprogramming somatic cells to prepare iPSCs, wherein the exogenously introduced two inducing factors are Oct4 and Nanog, and the three chemical inducing agents consist of a TGFβ receptor inhibitor such as 616452, a cyclic AMP (cAMP) agonist such as Forskolin, and a glycogen synthase kinase (GSK) inhibitor such as TD114-2. Specifically, the Oct4 and Nanog can be introduced into somatic cells in the form of their DNAs, RNAs or proteins.

In the present invention, different forms of reprogramming-inducing factors in combination with the three small molecule compounds as chemical inducing agents can significantly improve the reprogramming efficiency of human somatic cells and reduce the tumorigenicity of the obtained iPSCs.

DETAILED DESCRIPTION

Figure 1:
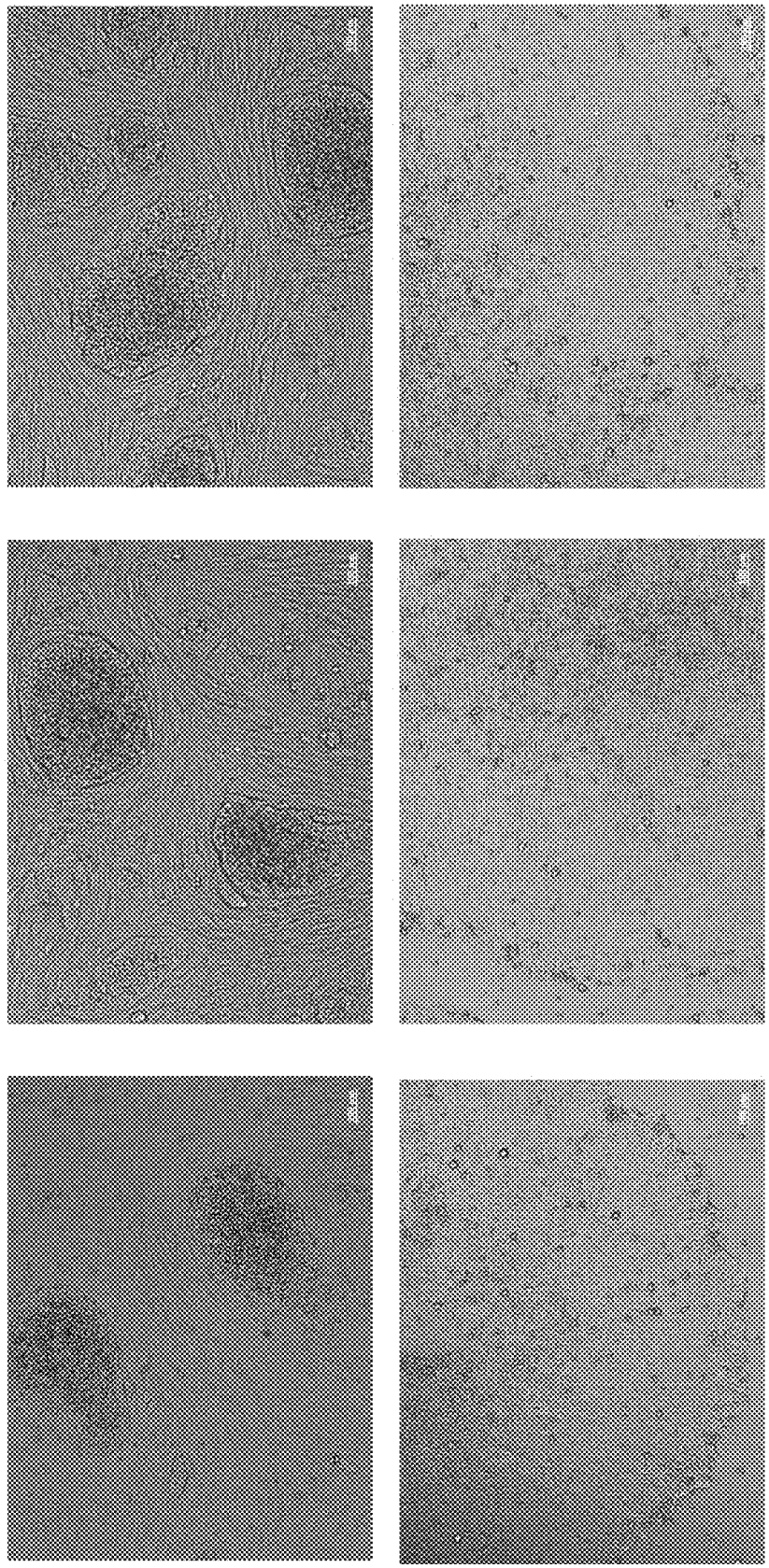
FIG. 1A shows two brightfield images of iPSCs obtained by the methods as described in Example 1, in which the upper panel of FIG. 1A shows the iPSC colonies after reprogramming for about 12 days, and the lower panel of FIG. 1A shows the iPSC colonies after picking single colonies and inoculating into a feeder-free system for culture.
FIG. 1B shows two brightfield images of iPSCs obtained by the methods as described in Example 2, in which the upper panel of FIG. 1B shows the iPSC colonies after reprogramming for about 12 days, and the lower panel of FIG. 1B shows the iPSC colonies after picking single colonies and inoculating into a feeder-free system for culture.
FIG. 1C shows two brightfield images of iPSCs obtained by the methods as described in Example 3, in which the upper panel of FIG. 1C shows the iPSC colonies after reprogramming for about 12 days, and the lower panel of FIG. 1C shows the iPSC colonies after picking single colonies and inoculating into a feeder-free system for culture.

In the method of the present invention, only Oct4 and Nanog are used as reprogramming-inducing factors, and reprogramming is performed by introducing them into somatic cells. Both Oct4 and Nanog are transcription factors that play important roles in maintaining pluripotency. A variety of transcription factors have been identified in the prior art that can be used to induce the reprogramming of somatic cells into induced pluripotent stem cells, such as Oct4, c-Myc, Sox2, and Klf4 consisting the Yamanaka four-factor combination as described above, and Oct4, Sox2, Nanog and Lin28 consisting the James Thomson four-factor combination. But the method of the present invention uses only Oct4 in the Yamanaka four factors and Nanog in the James Thomson four factors. In other words, the method of the present invention does not use any transcription factors other than Oct4 and Nanog as reprogramming-inducing factors.

Oct4 and Nanog can be introduced by a method known in the art for introducing transcription factors. Such methods include, but are not limited to, infecting somatic cells by introducing virus comprising recombinant DNA vector(s), mRNAs or RNAs of the nucleotides encoding Oct4 and Nanog so as to allow the expression of Oct4 and Nanog inducing factors, or by directly introducing Oct4 and Nanog in the form of proteins into somatic cells.

In one embodiment of the method of the present invention, the two reprogramming-inducing factors are introduced into somatic cells in the form of DNA. Specifically, a nucleotide sequence encoding Oct4 and a nucleotide sequence encoding Nanog can be introduced into somatic cells. In a specific embodiment, the nucleotide sequence encoding Oct4 comprises the nucleotide sequence as shown in SEQ ID NO: 6 or is consisted of the nucleotide sequence as shown in SEQ ID NO: 6; or comprises a nucleotide sequence that has at least 90% homology to the nucleotide sequence of SEQ ID NO: 6 and encodes Oct4; or is consisted of a nucleotide sequence that has at least 90% homology to the nucleotide sequence of SEQ ID NO: 6 and encodes Oct4. In a specific embodiment, the nucleotide sequence encoding Nanog comprises the nucleotide sequence as shown in SEQ ID NO: 15 or is consisted of the nucleotide sequence as shown in SEQ ID NO: 15; or comprises a nucleotide sequence that has at least 90% homology to the nucleotide sequence of SEQ ID NO: 15 and encodes Nanog; or is consisted of a nucleotide sequence that has at least 90% homology to the nucleotide sequence of SEQ ID NO: 15 and encodes Nanog.

The nucleotide sequence encoding Oct4 and the nucleotide sequence encoding Nanog can be placed in the same vector or in different vectors. When placed in the same vector, the nucleotide sequence encoding Oct4 and the nucleotide sequence encoding Nanog may be under the control of the same or different regulatory sequences. Regulatory sequences can be selected according to the type of target cell. In a specific embodiment, the nucleotide sequence encoding Oct4 and the nucleotide sequence encoding Nanog are placed in the same vector, such as pcDNA3.1. Additional elements, such as the coding sequence of EBNA1 and OriP sequence, may be comprised in the recombinant vector to increase the efficiency of plasmid replication in cells. In a specific embodiment, the sequence of the recombinant vector used in the present invention is shown in SEQ ID NO: 13 or SEQ ID NO: 24.

Methods for delivering vector(s) comprising nucleotides of interest into somatic cells are known in the art and include, but are not limited to, electroporation, gene gun, lipofection, calcium-mediated transfection. In a specific embodiment, electroporation is used.

In the method of the present invention, the above-mentioned inducing factors Oct4 and Nanog can be expressed in vitro to obtain corresponding proteins, which are then introduced into differentiated cells, thereby achieving the object of the present invention. Techniques for introducing proteins into cells are well known in the art and include, but are not limited to, Tat-delivery and related techniques, electroporation (nucleofection), protein and cellular ligand binding.

Those of ordinary skill in the art can also understand that the DNA sequences of the above-mentioned Oct4 and Nanog inducing factors can be transcribed in vitro, and the obtained mRNAs are directly introduced into differentiated cells to express the corresponding proteins in the cells, thus achieving the purpose of the present invention. Reprogramming can also be performed by infecting somatic cells with Sendai Virus comprising RNAs of the two inducing factors. Sendai Virus is a non-integrating virus that will not integrate into the genome of infected cells and thus has relatively high safety.

After introduction of the reprogramming-inducing factors Oct4 and Nanog into somatic cells, cells were cultured in the presence of one or more of a TGFβ receptor inhibitor, a cyclic AMP (cAMP) agonist, and a glycogen synthase kinase (GSK) inhibitor as chemical inducing agent(s) to generate iPSCs. In preferred embodiments, a TGFβ receptor inhibitor, a cyclic AMP (cAMP) agonist, and a glycogen synthase kinase (GSK) inhibitor are used.

In a preferred embodiment, the TGFβ receptor inhibitor is 616452, whose chemical name is 2-[3-(6-methyl-2-pyridinyl)-1H-pyrazol-4-yl]-1,5-naphthyridine (CAS No: 446859-33-2). Preferably, the TGFβ receptor inhibitor is used at a working concentration of 0.1-20 µM, more preferably 5-10 µM, still more preferably 5 µM. For example, the TGFβ receptor inhibitor is added to the medium at such concentration.

In a preferred embodiment, the cyclic AMP (cAMP) agonist is Forskolin, whose chemical name is [(3R,4aR,5S,6S,6aS,10S,10aR,10bS)-3-ethenyl-6,10,10b-trihydroxy-3,4a,7,7,10a-pentamethyl-1-oxo-5,6,6a,8,9,10-hexahydro-2H-benzo[f]chromen-5-yl]acetate (CAS No: 66575-29-9). Preferably, the cAMP agonist is used at a working concentration of 0.1-50 µM, more preferably 2-20 µM, still more preferably 10 µM. For example, the cAMP agonist is added to the medium at such concentration.

In a preferred embodiment, the glycogen synthase kinase (GSK) inhibitor is TD114-2, whose chemical name is 6,7,9,10,12,13,15,16,18,19-Decahydro-5,29:20,25-dimetheno-26H-dibenzo [n,t]pyrrolo[3,4-q][1,4,7,10,13,22] tetraoxa diazacyclotetracosine-26,28(27H)-dione (CAS No: 436866-52-3). Preferably, the GSK inhibitor is used at a working concentration of 0.1-20 µM, more preferably 2-10 µM, still more preferably 5 µM. For example, the GSK inhibitor is added to the medium at such concentration.

The medium used in the method of the present invention can be selected by a person skilled in the art based on existing knowledge depending on the type of cells to be cultured.

EXAMPLES

In order to facilitate understanding of the present invention, the technical solutions of the present invention will be further exemplified below through specific examples. Those of ordinary skill in the art can understand that the present invention is not limited to the described examples, and those of ordinary skill in the art can make modifications to the examples based on the teachings of the disclosure. Such modifications are also included within the scope of the present invention as defined by the appended claims.

The experimental methods in the following examples are conventional methods unless otherwise specified.

Example 1. Inducing the Reprogramming of Skin Cells by Using a Vector Encoding Reprogramming Factors 1.1 Human-derived skin tissue was placed into a petri dish, and was quickly and repeatedly rinsed for 4 times with phosphate buffered saline (PBS) pre-cooled at 4° C.

1.2 The skin tissue was processed with sterilized ophthalmic scissors and a scalpel to remove the subcutaneous white fat, remove the epidermis and subcutaneous tissue, and leave the dermis layer to obtain pretreated skin tissues. The pretreated skin tissue was transferred in the medium, and cut into small pieces to obtain skin tissue pieces with neat edges.

1.3 3 mL of fetal bovine serum (FBS) was evenly added to each well of a 6-well cell culture plate. The skin tissue pieces were added and incubated in the incubator for 0.5-1 h to make the tissues adhere to the bottom of the culture plate.

1.4 1 mL of DMEM (Gibco) medium comprising 20% (v/v) FBS was added to each well of the 6-well cell culture plate, and the plate was put back into the incubator for culture.

1.5 The medium was exchanged when fibroblasts migrated out of the skin tissue pieces as observed under the microscope. The amount of DMEM medium was increased to 3 mL, and the medium was exchanged every 1-3 days.

1.6 When the fibroblasts converged to the edge of each well, the spent medium was discarded. After washing twice with PBS, 1 mL of 0.25% trypsin-EDTA (GIBCO) was added, and the plate was placed in a cell culture incubator for about 4-6 min.

When the cells became round, detached and floated, DMEM medium comprising 20% (v/v) FBS was immediately added to terminate the digestion. The cells were pipetted several times gently and transferred into a 15 mL centrifuge tube, and centrifuged at 200 g for 3 min. The supernatant was aspirated and discarded. The cell culture medium was added to the tube and mixed thoroughly. The cells were transferred to a culture flask, which was placed in a cell incubator to continue culturing.

1.7 When the second-generation skin fibroblasts reached 80%-90% confluence, the old medium was discarded. The cells were washed twice with PBS, followed by digestion via adding 3 mL of 0.25% trypsin-EDTA (Gibco), until the cells were dispersed. DMEM medium comprising 20% (v/v) FBS was added to stop digestion. The cells were pipetted several times gently and transferred into a 15 mL centrifuge tube, and centrifuged at 200 g for 3 min. The supernatant was discarded. A suitable amount of PBS was added to resuspend the cells, which were counted by using a hemocytometer.

1.8 About 8×10⁵ skin fibroblasts were taken for centrifuge at 200 g for 3 min. The cells were washed twice with PBS and once with OPTI-MEM (Gibco). The supernatant was discarded. Corresponding electroporation reagents were added according to the instructions of the Celetrix Kit. Cells were resuspended. The reprogramming vector comprising the inducing factors Oct4 and Nanog were added to the cell suspension, mixed well and transferred to an electroporation cuvette. The electroporation cuvette was placed in an electroporation apparatus, and electroporation was conducted at 430 V, 30 ms.

Specifically, the reprogramming vector was constructed as follows: ① Using the plasmid (Addgen #20922) as the template, KOD-Plus-Neo (TOYOBO #KOD-401) high-fidelity enzyme and primers F1/R1, F2/R2, F3/R3 were used to perform the amplification, resulting in the fragment of EF-1α promoter, Oct4 coding sequence and Nanog coding sequence, respectively (see Table 1 below for the primer sequences and the sequences obtained by the amplification). ② Using the pcDNA3.1(-) plasmid as template, amplification was performed by using KOD-Plus-Neo (TOYOBO #KOD-401) high-fidelity enzyme and primers F4/R4 to obtain the pcDNA3.1 fragment (see Table 1 below for the primer sequences and the sequence obtained by the amplification). ③ Using NEBuilder HiFi DNA Assembly Bundle for Large Fragments (NEB #E2623), the pcDNA3.1 was ligated with the EF-1α promoter, the Oct4 coding sequence and the Nanog coding sequence by homologous recombination, so that the coding sequences of Oct4 and Nanog were under the control of the EF-1α promoter, resulting in the target vector, namely pcDNA3.1-EF-Oct4-Nanog (SEQ ID NO: 13).

1.9 After the electroporation, the electroporation cuvette was taken out. The cell suspension was quickly aspirated and added to Matrigel (Corning)-coated cell culture plate comprising 2 mL of DMEM medium comprising 20% (v/v) FBS added in advance. On Day 2, the medium was changed to 2-3 mL of TeSR-E7 medium (Stem Cell Technologies). Static culture was conducted at 37° C. in cell incubator. The medium was completely exchanged every day since then. Starting from Day 2, medium being used was supplemented with a combination of small molecule compounds, in which the working concentrations of the compounds were as follows. The working concentration of TGFβ receptor inhibitor 616452 was 5 µM. The working concentration of cyclic AMP (cAMP) agonist Forskolin was 10 µM. The working concentration of glycogen synthase kinase (GSK) inhibitor TD114-2 was 5 µM.

After reprogramming for about 12 days, iPSC colonies with cell morphology distinct from those of skin fibroblasts were observed (see the upper panel of FIG. 1A). Single colonies were picked and inoculated into a feeder-free system for culture. These iPSC colonies formed by cells with relatively small size were compact and well-defined iPSC colonies, in which the cells had a relatively large nuclei and high nucleocytoplasmic ratio, showing a typical iPSC morphology (see the lower panel of FIG. 1A).

Example 2. Inducing the Reprogramming of Skin Cells by Using a Vector Encoding Reprogramming Factors The same protocol was used as described in steps 1.1-1.9 of Example 1. Fibroblasts derived from human skin tissue were used for conducting the method of the present invention. As compared to Example 1, the construction of the reprogramming vector in step 1.8 is different. On the basis of the construct of Example 1, EBNA1 and OriP elements were added, so that the replication efficiency of the plasmid could be enhanced in somatic cells based on the EBNA1/OriP system. The construction method is described in detail as follows.

① Using plasmid (Addgen #20922) as the template, KOD-Plus-Neo (TOYOBO #KOD-401) high-fidelity enzyme and primers F5/R5, F6/R6, F7/R7, F8/R8, F9/R9 were used to perform the amplification, resulting in the fragment of EF-1α promoter, Oct4 coding sequence, Nanog coding sequence, EBNA1 coding sequence and OriP sequence, respectively (see Table 1 below for the primer sequences and the sequences obtained by the amplification). ② Using the pcDNA3.1(-) plasmid as the template, amplification was performed by using KOD-Plus-Neo (TOYOBO #KOD-401) high-fidelity enzyme and primers F10/R10 to obtain the pcDNA3.1 fragment (see Table 2 below for the primer sequences and the sequence obtained by the amplification). ③ Using NEBuilder HiFi DNA Assembly Bundle for Large Fragments (NEB #E2623), the pcDNA3.1 was ligated with the EF-1α promoter, the Oct4 coding sequence, the Nanog coding sequence, the EBNA1 coding sequence and the OriP sequence by homologous recombination, resulting in the target vector, namely pcDNA3.1-EF-Oct4-Nanog-EBNA1-OriP (SEQ ID NO: 24).

After reprogramming for about 12 days, iPSC colonies with cell morphology distinct from those of skin fibroblasts were observed (see the upper panel of FIG. 1B). Single colonies were picked and inoculated into a feeder-free system for culture. These iPSC colonies formed by cells with relatively small size were compact and well-defined iPSC colonies, in which the cells had a relatively large nuclei and high nucleocytoplasmic ratio, showing a typical iPSC morphology (see the lower panel of FIG. 1B).

Example 3. Inducing the Reprogramming of Skin Cells by Using a Virus Comprising RNAs of Reprogramming-Inducing Factors The same protocol was used as described in steps 1.1-1.6 of Example 1. Fibroblasts derived from human skin tissue were used for conducting the method of the present invention. Different from steps 1.7-1.9 of Example 1, reprogramming of iPSCs was performed by using a virus comprising RNAs of reprogramming-inducing factors as described in step 3.7 below.

3.7 When the second-generation skin fibroblasts reached 80%-90% confluence, Sendai Virus comprising Oct4 and Nanog reprogramming-inducing factors was mixed with the cells and cultured for 2 days. The medium was discarded. 2 mL of DMEM medium with 20% (v/v) FBS was added to culture, and the medium was changed every other day. After culturing for 5 days, 1 mL of 0.25% trypsin-EDTA (GIBCO) was added, followed by culture in a cell incubator for about 4~6 min. When the cells became round, detached and floated, they were added to Vitronectin (Gibco)-coated cell culture plates for culture. Starting from Day 2 of the culture, medium being used was supplemented with a combination of small molecule compounds, in which the working concentrations of the compounds were as follows. The working concentration of TGFβ receptor inhibitor 616452 was 5 μM. The working concentration of cyclic AMP (cAMP) agonist Forskolin was 10 μM. The working concentration of glycogen synthase kinase (GSK) inhibitor TD114-2 was 5 μM.

After reprogramming for about 12 days, iPSC colonies with cell morphology distinct from those of skin fibroblasts were observed (see the upper panel of FIG. 1C). Single colonies were picked and inoculated into a feeder-free system for culture. These iPSC colonies formed by cells with relatively small size were compact and well-defined iPSC colonies, in which the cells had a relatively large nuclei and high nucleocytoplasmic ratio, showing a typical iPSC morphology (see the lower panel of FIG. 1C).

Example 4. Identification of iPSCs Obtained by Reprogramming Skin Fibroblasts

The iPSCs obtained by reprogramming skin fibroblasts were characterized and identified using different methods, including flow cytometry, immunofluorescence staining and quantitative PCR (qPCR).

Figure 2:
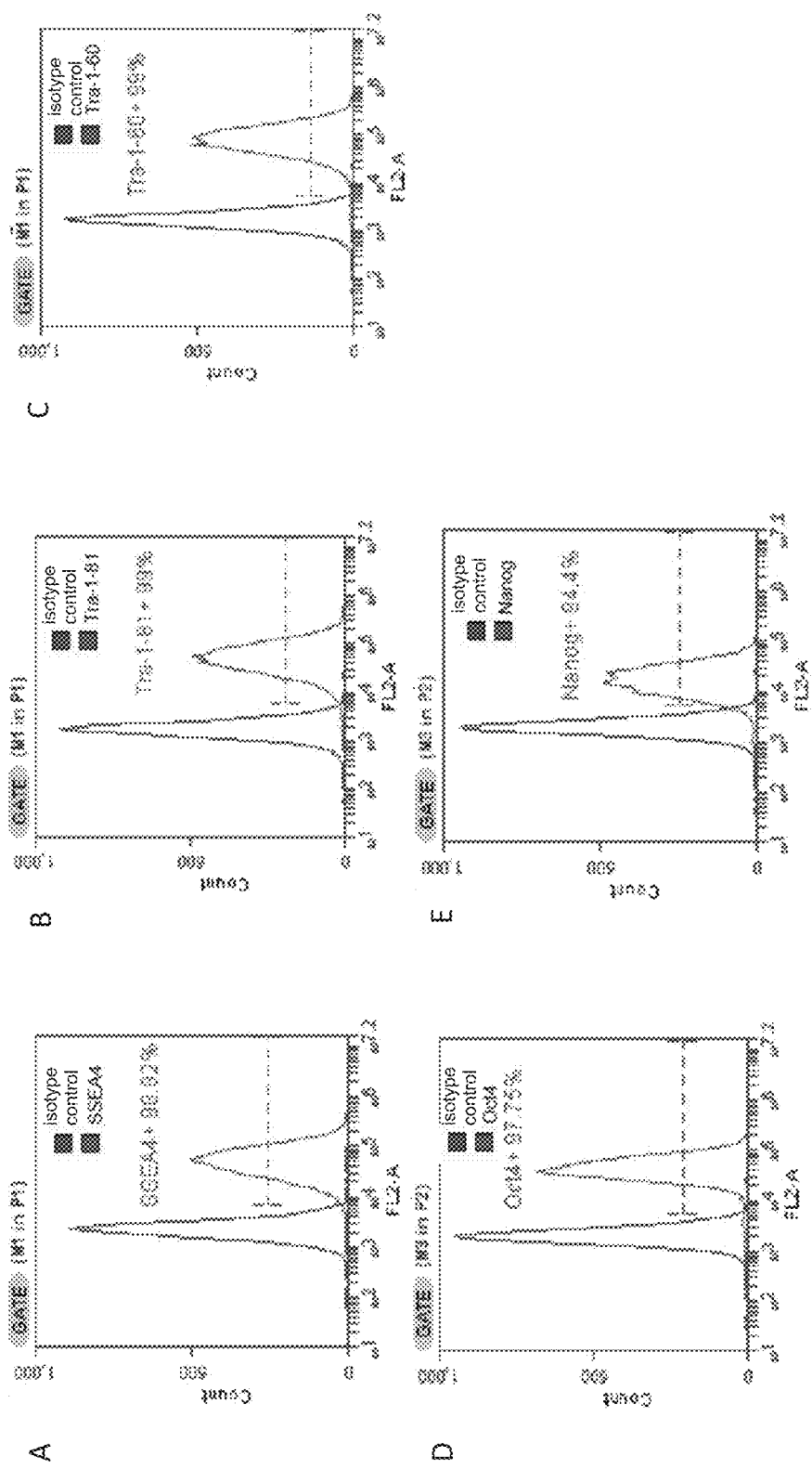
FIGS. 2A-E are the detection results of flow cytometry, showing the expression of pluripotent cell markers by iPSCs obtained by reprogramming of skin fibroblasts. (A) SSEA4; (B) Tra-1-81; (C) Tra-1-60; (D) Oct4; (E) Nanog.

The obtained iPSCs were analyzed by flow cytometry for the following molecular markers: SSEA4, Tra-1-81, Tra-1-60, Oct4 and Nanog. As shown in FIG. 2, the iPSCs obtained by the method of the present invention expressed the markers of human pluripotent stem cells including SSEA4, Tra-1-81, Tra-1-60, Oct4 and Nanog, which proved that the obtained cells possessed the characteristics of pluripotent stem cells.

Figure 3:
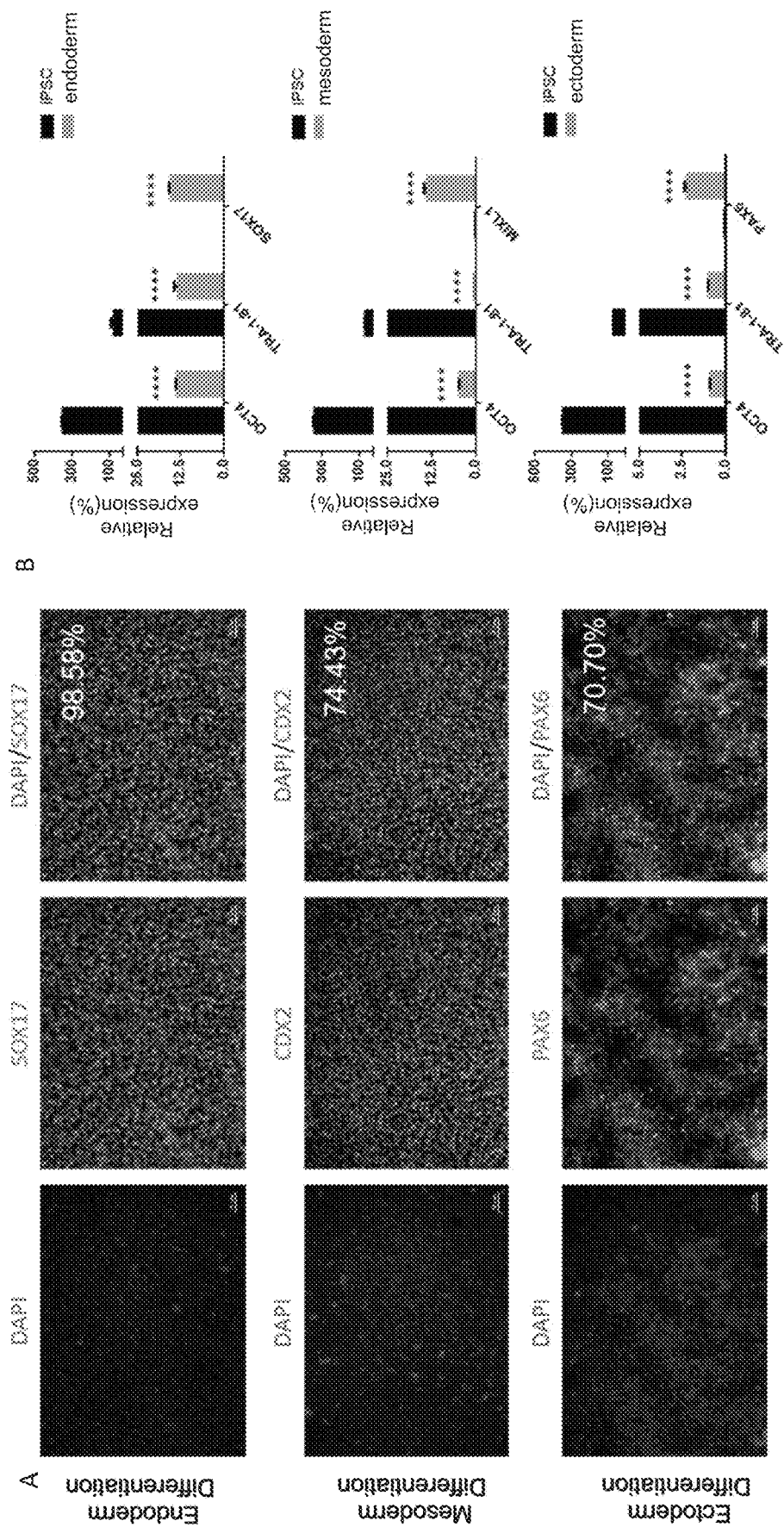
FIGS. 3A-B show the results of (A) immunofluorescence staining and (B) qPCR identification of differentiation of three germ layers from iPSCs obtained by reprogramming skin fibroblasts.

To verify the totipotency, the obtained iPSCs were induced to differentiate into three germ layers in vitro. The expression of molecular markers specific for the three germ layers was detected by immunofluorescence staining and qPCR. As shown in FIG. 3A, results of the immunofluorescence experiments using three markers (endoderm: SOX17; mesoderm: CDX2; ectoderm: PAX6) showed that the obtained iPSCs could differentiate into cells of all three germ layers. FIG. 3B shows the expression of molecular markers specific for three germ layers (endoderm: SOX17, mesoderm: MIXL1, and ectoderm: PAX6) detected by qPCR, in which the iPSCs expressed the molecular markers of pluripotent stem cell, OCT4 and TRA-1-81, at high levels (consistent with the aforementioned results of flow cytometry assay), while cells differentiated into three germ layers expressed the molecular markers specific for each germ layer (****$p<0.0001$, Student's t-test). These results indicated that the obtained iPSCs were totipotent.

Example 5. Inducing the Reprogramming of Peripheral Blood Cells by Using a Vector Encoding Reprogramming Factors 5.1 10 mL of human peripheral blood was collected, from which the erythroid progenitor cells were enriched and expanded by using RosetteSep™ kit and SepMate™ kit (Stem Cell Technologies). Specifically, 10 mL of blood was transferred from the blood collection tube to a regular centrifuge tube, to which 50 μL of RosetteSep™ Human Progenitor Cell Basic Pre-Enrichment Cocktail was added and mixed thoroughly. Then the tubes were placed at room temperature for 10 min.

5.2 3.5 mL of Lymphoprep™ was added to a SepMate centrifuge tube along the central hole. After incubating at room temperature for 10 minutes, 10 mL of PBS+2% FBS was added and mixed thoroughly. 5 mL of blood was added along the wall of the SepMate centrifuge tube Immediately after centrifuge at 1200 g for 10 min, the yellow supernatant was poured carefully into a new regular centrifuge tube (be careful not to pour in the unwanted cells at bottom), and centrifuged at 300 g for 8 min.

5.3 After centrifugation, the supernatant was discarded. The cells were resuspended with 0.5 mL of StemSpan™ SFEM II medium and counted for the total number. 2 mL of cells at a density of $5\times10^6$/mL was inoculated into each well of a 6-well plate, and cultured at 37° C., 5% $CO_2$ in cell incubator.

5.4 Day 1: the cell suspension was transferred to a new 6-well plate to remove adherent unwanted cells. Each well was supplemented with 0.5 mL StemSpan™ SFEM II medium, and incubated at 37° C., 5% $CO_2$ in cell incubator.

5.5 Day 2, Day 4, Day 6 and Day 8: Cell suspension from each well was collected into a centrifuge tube. Centrifuge was conducted at 400 g for 5 min, and the supernatant was discarded. StemSpan™ SFEM II medium was added to resuspend the cells. After pipetting for 3-4 times, 2 mL was inoculated into each well of a new 6-well plate, shaken thoroughly and cultured at 37° C., 5% $CO_2$ in cell incubator.

5.6 Day 9: The number of erythroid progenitor cells significantly increased. Further, the erythroid progenitor cells rapidly enriched on Day 10. When the number of cells reached $2\times10^6$, electroporation could be performed. The cell suspension was collected and centrifuged at 400 g for 5 min. The supernatant was discarded. According to the instructions of the Celetrix Kit, the corresponding electroporation reagents were added to resuspend the cells. Into the cell suspension, the reprogramming vector comprising inducing factors Oct4 and Nanog as constructed in Example 1, namely pcDNA3.1-EF-Oct4-Nanog (SEQ ID NO: 13), was added. After mixing thoroughly, the mixture was added to a electroporation cuvette, which was placed in electroporation apparatus to perform the electroporation at 820 V, 20 ms.

5.7 After the electroporation, the electroporation cuvette was taken out. The cell suspension was quickly aspirated and added to Matrigel (Corning)-coated cell culture plate comprising StemSpan™ SFEM II added in advance. On Day 2, 1 mL StemSpan™ SFEM II medium was supplemented to each well. Static culture was conducted at 37° C. in cell incubator. On Day 3 and Day 5, 1 mL ReproTeSR medium (Stem Cell Technologies) was supplemented to each well. On Day 7, it could be observed that cells began to grow adherent to the wall. The spent medium was discarded. Afterwards, the medium was replaced with 2 mL of fresh ReproTeSR medium for each well every day. Starting from Day 2, medium being used was supplemented with a combination of small molecule compounds, in which the working concentrations of the compounds were as follows. The working concentration of TGFβ receptor inhibitor 616452 was 5 μM. The working concentration of cyclic AMP (cAMP) agonist Forskolin was 10 μM. The working concentration of glycogen synthase kinase (GSK) inhibitor TD114-2 was 5 μM. After reprogramming for about 12 days, iPSC colonies derived from adherent growth of the cell mass in suspension culture could be observed (see the upper panel of FIG. 4A). Single colonies were picked and inoculated into a feeder-free system for culture. These iPSC colonies formed by cells with relatively small size were compact and well-defined iPSC colonies, in which the cells had a relatively large nuclei and high nucleocytoplasmic ratio, showing a typical iPSC morphology (see the lower panel of FIG. 4A).

Example 6. Inducing the Reprogramming of Peripheral Blood Cells by Using a Vector Encoding Reprogramming Factors The same protocol was used as described in steps 5.1-5.7 of Example 5. Erythroid progenitor cells derived from human peripheral blood were used for conducting the method of the present invention. Different from Example 5, the reprogramming vector used in step 5.6 was replaced by the reprogramming vector comprising inducing factors Oct4 and Nanog as constructed in Example 2, namely pcDNA3.1-EF-Oct4-Nanog-EBNA1-OriP.

Figure 4:
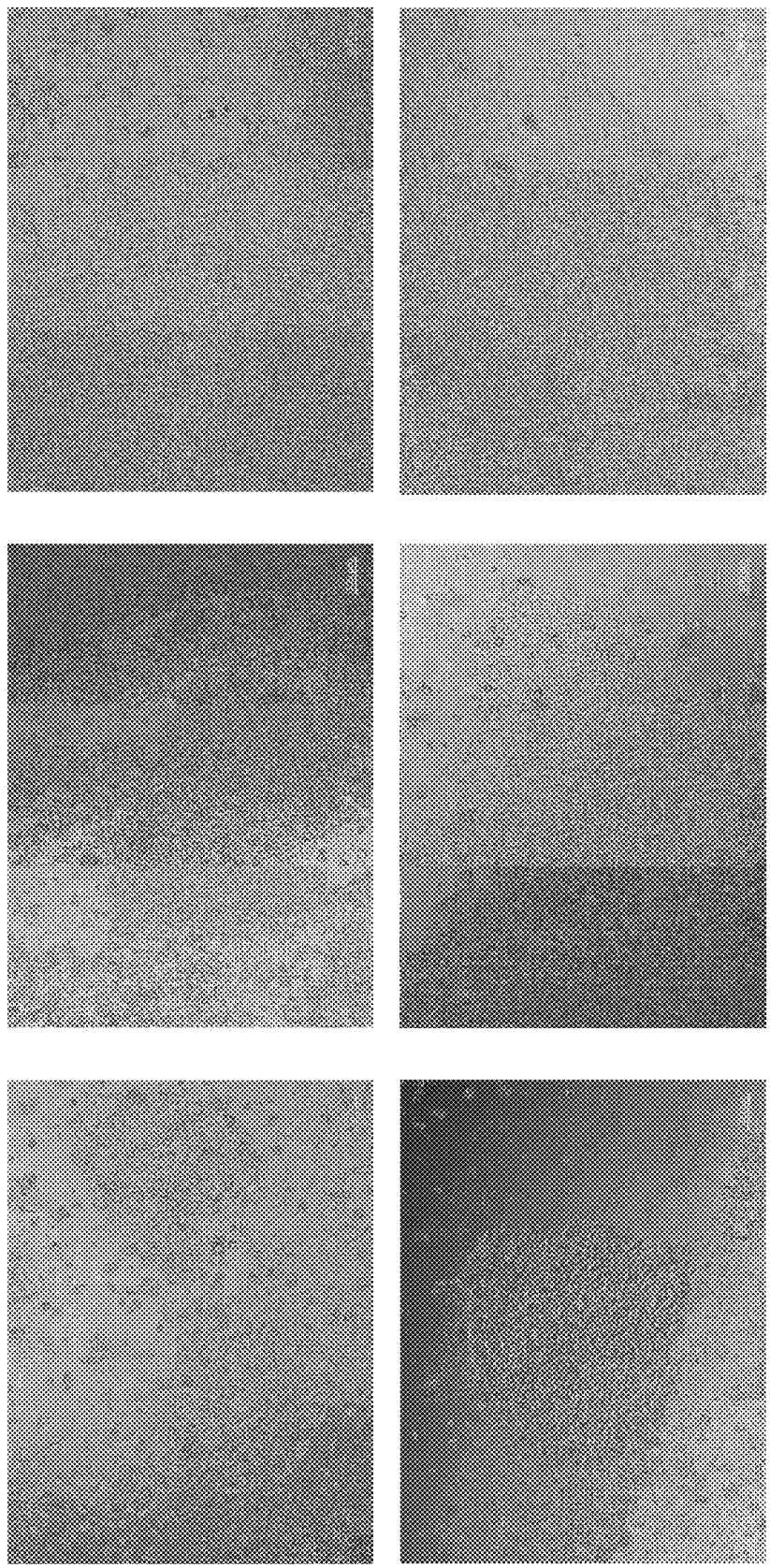
FIG. 4A shows two brightfield images of iPSCs obtained by the methods as described in Example 5, in which the upper panel of FIG. 4A shows the iPSC colonies after reprogramming for about 12 days, and the lower panel of FIG. 4A shows the iPSC colonies after picking single colonies and inoculating into a feeder-free system for culture.
FIG. 4B shows two brightfield images of iPSCs obtained by the methods as described in Example 6, in which the upper panel of FIG. 4B shows the iPSC colonies after reprogramming for about 12 days, and the lower panel of FIG. 4B shows the iPSC colonies after picking single colonies and inoculating into a feeder-free system for culture.
FIG. 4C shows two brightfield images of iPSCs obtained by the methods as described in Example 7, in which the upper panel of FIG. 4C shows the iPSC colonies after reprogramming for about 12 days, and the lower panel of FIG. 4C shows the iPSC colonies after picking single colonies and inoculating into a feeder-free system for culture.

After reprogramming for about 12 days, iPSC colonies derived from adherent growth of the cell mass in suspension culture could be observed (see the upper panel of FIG. 4B). Single colonies were picked and inoculated into a feeder-free system for culture. These iPSC colonies formed by cells with relatively small size were compact and well-defined iPSC colonies, in which the cells had a relatively large nuclei and high nucleocytoplasmic ratio, showing a typical iPSC morphology (see the lower panel of FIG. 4B).

Example 7. Inducing the Reprogramming of Peripheral Blood Cells by Using a Virus Comprising RNAs of Reprogramming-Inducing Factors The same protocol was used as described in steps 5.1-5.5 of Example 5. Erythroid progenitor cells derived from human peripheral blood were used for conducting the method of the present invention. Different from steps 5.6-5.7 of Example 5, reprogramming of iPSCs was performed by using a virus comprising RNAs of reprogramming-inducing factors as described in step 7.6 below.

7.6 On Day 9: The number of erythroid progenitor cells significantly increased. The cell suspension was collected and centrifuged at 400 g for 5 min. The supernatant was discarded. Sendai Virus comprising Oct4 and Nanog reprogramming-inducing factors in the form of RNAs was added to the cells and mixed. The cells were cultured for 2 days. The medium was discarded. 2 mL of ReproTeSR medium was added. Afterwards, the medium was replaced with 2 mL of fresh ReproTeSR medium for each well every day. Starting from Day 2, medium was supplemented with a combination of small molecule compounds, in which the working concentrations of the compounds were as follows. The working concentration of TGFβ receptor inhibitor 616452 was 5 μM. The working concentration of cyclic AMP (cAMP) agonist Forskolin was 10 μM. The working concentration of glycogen synthase kinase (GSK) inhibitor TD114-2 was 5 μM. After reprogramming for about 12 days, iPSC colonies derived from adherent growth of the cell mass in suspension culture could be observed (see the upper panel of FIG. 4C). Single colonies were picked and inoculated into a feeder-free system for culture. These iPSC colonies formed by cells with relatively small size were compact and well-defined iPSC colonies, in which the cells had a relatively large nuclei and high nucleocytoplasmic ratio, showing a typical iPSC morphology (see the lower panel of FIG. 4C).

Example 8. Identification of iPSCs Obtained by Reprogramming Erythroid Progenitor Cells The iPSCs obtained by reprogramming erythroid progenitor cells were characterized and identified using different methods, including flow cytometry, immunofluorescence staining and quantitative PCR (qPCR).

Figure 5:
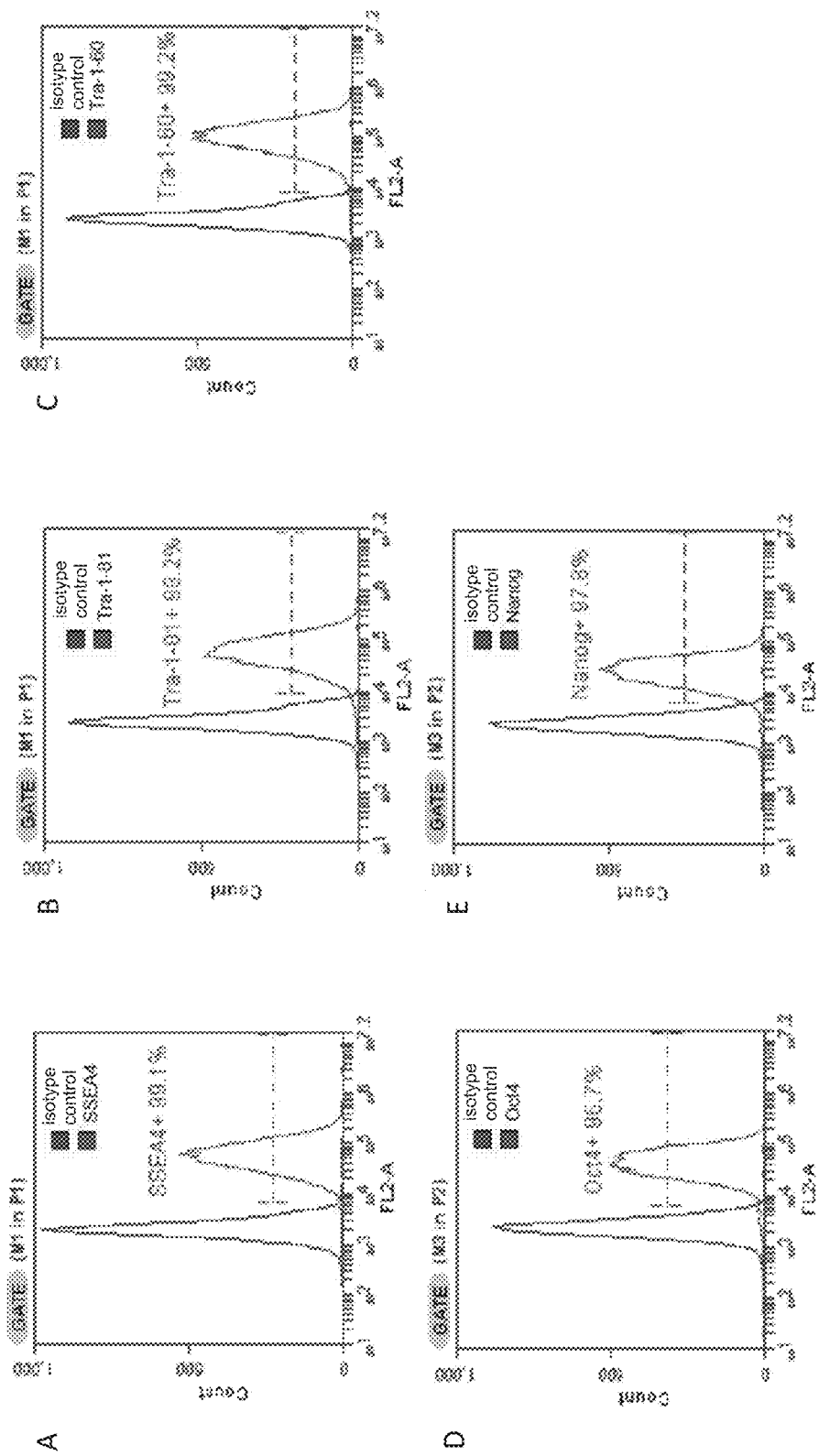
FIGS. 5A-E are the detection results of flow cytometry, showing the expression of pluripotent cell markers by iPSCs obtained by reprogramming of erythroid progenitor cells. (A) SSEA4; (B) Tra-1-81; (C) Tra-1-60; (D) Oct4; (E) Nanog.

The obtained iPSCs were analyzed by flow cytometry for the following molecular markers: SSEA4, Tra-1-81, Tra-1-60, Oct4 and Nanog. As shown in FIG. 5, the iPSCs obtained by the method of the present invention expressed the markers of human pluripotent stem cells including SSEA4, Tra-1-81, Tra-1-60, Oct4 and Nanog, which proved that the obtained cells possessed the characteristics of pluripotent stem cells.

Figure 6:
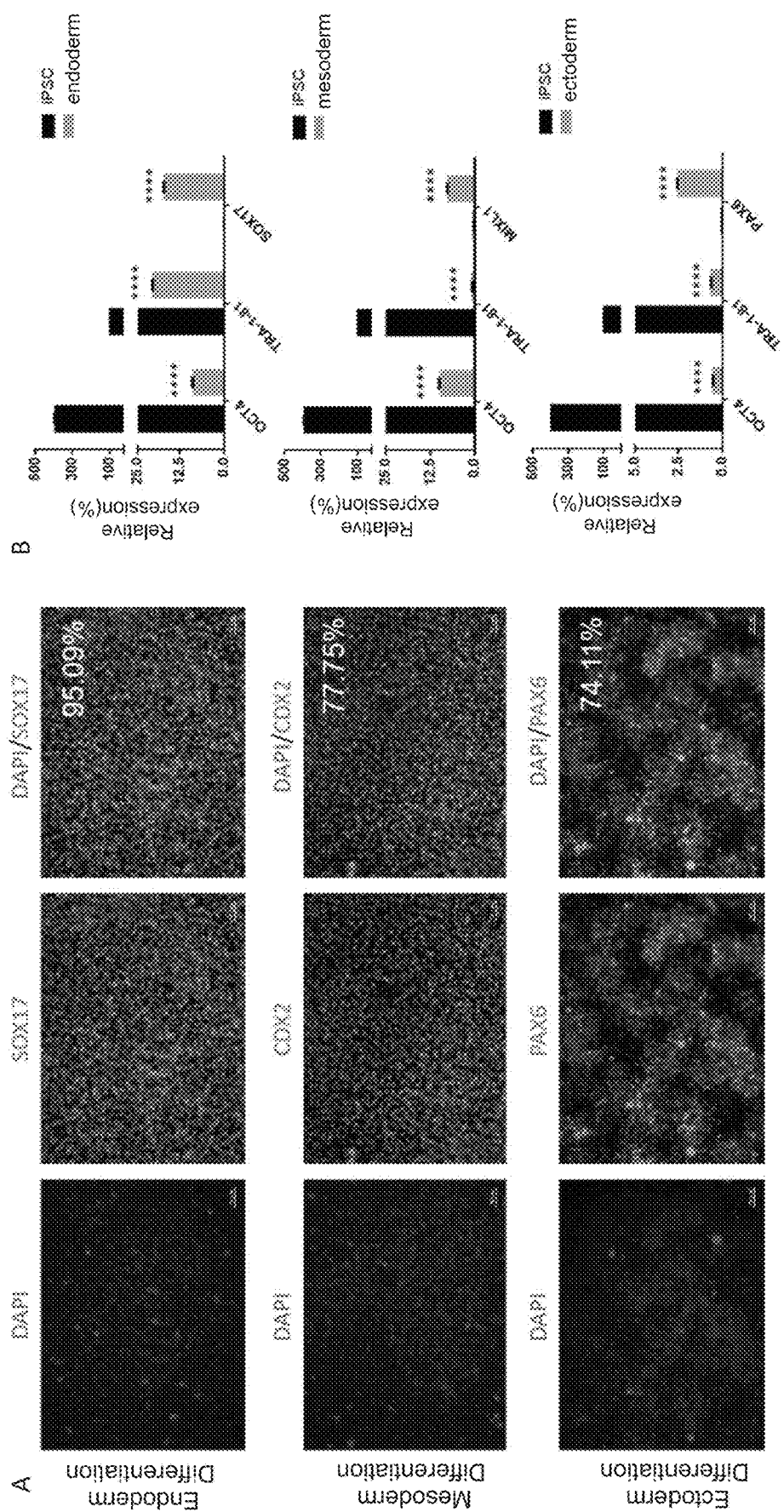
FIGS. 6A-B show the results of (A) immunofluorescence staining and (B) qPCR identification of differentiation of three germ layers from iPSCs obtained by reprogramming erythroid progenitor cells.

To verify the totipotency, the obtained iPSCs were induced to differentiate into three germ layers in vitro. The expression of molecular markers specific for the three germ layers was detected by immunofluorescence staining and qPCR. As shown in FIG. 6A, results of the immunofluorescence experiments using three markers (endoderm: SOX17; mesoderm: CDX2; ectoderm: PAX6) showed that the obtained iPSCs could differentiate into cells of all three germ layers. FIG. 6B shows the expression of molecular markers specific for three germ layers (endoderm: SOX17, mesoderm: MIXL1, and ectoderm: PAX6) detected by qPCR, in which the iPSCs expressed the molecular markers of pluripotent stem cell, OCT4 and TRA-1-81, at high levels (consistent with the aforementioned results of flow cytometry assay), while cells differentiated into three germ layers expressed the molecular markers specific for each germ layer (****$p<0.0001$, Student's t-test). These results indicated that the obtained iPSCs were totipotent.

TABLE 1

| Products of PCR amplification | | | | | |
|---|---|---|---|---|---|
| No. | Gene name | Primer name | 5'-3' | bp | Sequence after amplification |
| 1 | Ef-1α | F1 | SEQ ID NO: 1 | 35 | SEQ ID NO: 3 |
|  |  | R1 | SEQ ID NO: 2 | 35 |  |

TABLE 1-continued

Products of PCR amplification

| No. | Gene name | Primer name | 5'-3' | bp | Sequence after amplification |
|---|---|---|---|---|---|
| 2 | Oct4 | F2 | SEQ ID NO: 4 | 20 | SEQ ID NO: 6 |
|  |  | R2 | SEQ ID NO: 5 | 20 |  |
| 3 | Nanog | F3 | SEQ ID NO: 7 | 92 | SEQ ID NO: 9 |
|  |  | R3 | SEQ ID NO: 8 | 35 |  |
| 4 | pcDNA3.1 | F4 | SEQ ID NO: 10 | 20 | SEQ ID NO: 12 |
|  |  | R4 | SEQ ID NO: 11 | 20 |  |

TABLE 2

Products of PCR amplification

| No. | Gene name | Primer name | 5'-3' | bp | Sequence after amplification |
|---|---|---|---|---|---|
| 1 | EF-1α | F5, identical to F1 | SEQ ID NO: 1 | 35 | SEQ ID NO: 3 |
|  |  | R5, identical to R1 | SEQ ID NO: 2 | 35 |  |
| 2 | Oct4 | F6, identical to F2 | SEQ ID NO: 4 | 20 | SEQ ID NO: 6 |
|  |  | R6, identical to R2 | SEQ ID NO: 5 | 20 |  |
| 3 | Nanog | F7, identical to F3 | SEQ ID NO: 7 | 92 | SEQ ID NO: 15 |
|  |  | R7 | SEQ ID NO: 14 | 92 |  |

TABLE 2-continued

Products of PCR amplification

| No. | Gene name | Primer name | 5'-3' | bp | Sequence after amplification |
|---|---|---|---|---|---|
| 4 | EBNA1 | F8 | SEQ ID NO: 16 | 38 | SEQ ID NO: 18 |
|  |  | R8 | SEQ ID NO: 17 | 85 |  |
| 5 | OriP | F9 | SEQ ID NO: 19 | 101 | SEQ ID NO: 21 |
|  |  | R9 | SEQ ID NO: 20 | 34 |  |
| 6 | pcDNA3.1 | F10 | SEQ ID NO: 22 | 20 | SEQ ID NO: 23 |
|  |  | R10, identical to R4 | SEQ ID NO: 11 | 20 |  |

The method for preparing iPSCs of the present invention reduces the number of transcription factors required for reprogramming to two, reduces the tumorigenicity, and improves the transformation efficiency through the combination of three small molecule compounds. In general, the method of the present invention is simple, efficient and easy to operate. The iPSCs prepared by this method would be more suitable for clinical translations and applications.

The above are only the preferred embodiments of the present invention. It should be pointed out that for those skilled in the art, without departing from the principles of the present invention, several improvements and modifications can be made. These improvements and modifications should also be regarded as within the protection scope of the present invention.

The invention claimed is:

1. A method of generating mammalian induced pluripotent stem cells (iPSCs), the method comprising:
   (1) introducing one or more nucleic acids encoding the reprogramming-inducing factors Oct4 and Nanog into mammalian fibroblasts or mammalian erythroid progenitor cells to obtain reprogrammed fibroblasts or erythroid progenitor cells;
   (2) culturing the reprogrammed fibroblasts or erythroid progenitor cells obtained in step (1) in the presence of chemical inducing agents to obtain induced pluripotent stem cells (iPSCs), wherein the chemical inducing agents are consisting of a TGFB receptor inhibitor, a cyclic AMP (cAMP) agonist, and a glycogen synthase kinase (GSK) inhibitor,
   wherein only Oct4 and Nanog are used as reprogramming-inducing factors.

2. The method according to claim 1, wherein the reprogramming-inducing factors Oct4 and Nanog are introduced in the mammalian fibroblasts or mammalian erythroid progenitor cells in the form of DNA thereof or in the form of mRNA thereof.

3. The method according to claim 1, wherein the TGFβ receptor inhibitor is 616452, and/or the cyclic AMP (CAMP) agonist is Forskolin, and/or the glycogen synthase kinase (GSK) inhibitor is TD114-2.

4. The method according to claim 3, wherein the working concentration of the TGFB receptor inhibitor 616452 is 0.1-20 μM; and/or the working concentration of the cyclic AMP (CAMP) agonist Forskolin is 0.1-50 μM; and/or the working concentration of the glycogen synthase kinase (GSK) inhibitor TD114-2 is 0.1-20 μM.

5. The method according to claim 1, wherein the mammalian fibroblast or mammalian erythroid progenitor cell is isolated from skin cells, blood cells, urine cells, liver cells, epithelial cells, or gastric cells.

6. The method according to claim 1, wherein the mammalian fibroblasts or mammalian erythroid progenitor cells are isolated from human.

7. The method according to claim 1, wherein in step (1), the introducing one or more nucleic acids encoding the reprogramming-inducing factors Oct4 and Nanog into the mammalian fibroblasts or mammalian erythroid progenitor cells comprises introducing:
   a) a single recombinant vector comprising both nucleotide sequences encoding the reprogramming-inducing factors Oct4 and Nanog, or
   b) two recombinant vectors, wherein one recombinant vector comprises a nucleic acid sequence encoding Oct4 and the other recombinant vector comprises a nucleic acid sequence encoding Nanog.

8. The method according to claim 1, wherein in step (1), the introducing one or more nucleic acids encoding the reprogramming-inducing factors Oct4 and Nanog is performed by infecting the mammalian fibroblasts or mammalian erythroid progenitor cells with:
   a) a single recombinant Sendai virus comprising a nucleotide sequence encoding Oct4 and a nucleotide sequence encoding Nanog, or
   b) two recombinant Sendai viruses, wherein one virus comprises the nucleotide sequence encoding Oct4 and the other virus comprises the nucleotide sequence encoding Nanog.

9. The method according to claim 8, wherein at least one of the nucleotide sequence encoding Oct4 and the nucleotide sequence encoding Nanog is RNA.

10. The method according to claim 4, wherein the working concentration of 616452 is 5-10 μM.

11. The method according to claim 4, wherein the working concentration of 616452 is 5 μM.

12. The method according to claim 4, wherein the working concentration of Forskolin is 2-20 μM.

13. The method according to claim 4, wherein the working concentration of Forskolin is 10 μM.

14. The method according to claim 4, wherein the working concentration of TD114-2 is 2-10 μM.

15. The method according to claim 4, wherein the working concentration of TD114-2 is 5 μM.

* * * * *

SEQUENCE LISTING

<160> NUMBER OF SEQ ID NOS: 24

<210> SEQ ID NO 1
<211> LENGTH: 35
<212> TYPE: DNA
<213> ORGANISM: Artificial Sequence
<220> FEATURE:
<223> OTHER INFORMATION: Ef-1alpha F1 primer

<400> SEQUENCE: 1
atacgactca ctataggctc cggtgcccgt cagtg                35

<210> SEQ ID NO 2
<211> LENGTH: 35
<212> TYPE: DNA
<213> ORGANISM: Artificial Sequence
<220> FEATURE:
<223> OTHER INFORMATION: Ef-1alpha R1 primer

<400> SEQUENCE: 2
caggtgtccc gccatcacga cacctgaaat ggaag                35

<210> SEQ ID NO 3
<211> LENGTH: 1192
<212> TYPE: DNA
<213> ORGANISM: Artificial Sequence
<220> FEATURE:
<223> OTHER INFORMATION: Ef-1alpha amplicon

<400> SEQUENCE: 3
atacgactca ctataggctc cggtgcccgt cagtgggcag agcgcacatc gcccacagtc    60
cccgagaagt tggggggagg ggtcggcaat tgaaccggtg cctagagaag gtggcgcggg   120
gtaaactggg aaagtgatgt cgtgtactgg ctccgccttt ttcccgaggg tggggagaa   180

| | | |
|---|---|---|
| ccgtatataa gtgcagtagt cgccgtgaac gttcttttc gcaacgggtt tgccgccaga | 240 | |
| acacaggtaa gtgccgtgtg tggttcccgc gggcctggcc tctttacggg ttatggccct | 300 | |
| tgcgtgcctt gaattacttc cacctggctc cagtacgtga ttcttgatcc cgagctggag | 360 | |
| ccaggggcgg gccttgcgct ttaggagccc cttcgcctcg tgcttgagtt gaggcctggc | 420 | |
| ctgggcgctg gggccgccgc gtgcgaatct ggtggcacct tcgcgcctgt ctcgctgctt | 480 | |
| tcgataagtc tctagccatt taaaattttt gatgacctgc tgcgacgctt ttttctggc | 540 | |
| aagatagtct tgtaaatgcg ggccaggatc tgcacactgg tatttcggtt tttgggcccg | 600 | |
| cggccggcga cggggcccgt gcgtcccagc gcacatgttc ggcgaggcgg ggcctgcgag | 660 | |
| cgcggccacc gagaatcgga cggggtagt ctcaagctgg ccggcctgct ctggtgcctg | 720 | |
| gcctcgcgcc gccgtgtatc gccccgcccct gggcggcaag gctggcccgg tcggcaccag | 780 | |
| ttgcgtgagc ggaaagatgg ccgcttcccg gccctgctcc agggggctca aaatggagga | 840 | |
| cgcggcgctc gggagagcgg gcgggtgagt cacccacaca aaggaaaagg ccttttccgt | 900 | |
| cctcagccgt cgcttcatgt gactccacgg agtaccgggc gccgtccagg cacctcgatt | 960 | |
| agttctggag cttttggagt acgtcgtctt taggttgggg ggaggggttt tatgcgatgg | 1020 | |
| agtttcccca cactgagtgg gtggagactg aagttaggcc agcttggcac ttgatgtaat | 1080 | |
| tctcgttgga atttgccctt tttgagtttg gatcttggtt cattctcaag cctcagacag | 1140 | |
| tggttcaaag ttttttttctt ccatttcagg tgtcgtgatg gcgggacacc tg | 1192 | |

```
<210> SEQ ID NO 4
<211> LENGTH: 20
<212> TYPE: DNA
<213> ORGANISM: Artificial Sequence
<220> FEATURE:
<223> OTHER INFORMATION: OCT4 F2 primer

<400> SEQUENCE: 4
```

| | |
|---|---|
| atggcgggac acctggcttc | 20 |

```
<210> SEQ ID NO 5
<211> LENGTH: 20
<212> TYPE: DNA
<213> ORGANISM: Artificial Sequence
<220> FEATURE:
<223> OTHER INFORMATION: OCT4 R2 primer

<400> SEQUENCE: 5
```

| | |
|---|---|
| tcagtttgaa tgcatgggag | 20 |

```
<210> SEQ ID NO 6
<211> LENGTH: 1083
<212> TYPE: DNA
<213> ORGANISM: Artificial Sequence
<220> FEATURE:
<223> OTHER INFORMATION: OCT4 amplicon

<400> SEQUENCE: 6
```

| | |
|---|---|
| atggcgggac acctggcttc ggatttcgcc ttctcgcccc ctccaggtgg tggaggtgat | 60 |
| gggccagggg ggccggagcc gggctgggtt gatcctcgga cctggctaag cttccaaggc | 120 |
| cctcctggag ggccaggaat cgggccgggg gttgggccag gctctgaggt gtggggatt | 180 |
| cccccatgcc ccccgccgta tgagttctgt gggggggatgg cgtactgtgg gcccaggtt | 240 |
| ggagtggggc tagtgcccca aggcggcttg gagacctctc agcctgaggg cgaagcagga | 300 |
| gtcggggtgg agagcaactc cgatggggcc tccccggagc cctgcaccgt caccctggt | 360 |

```
gccgtgaagc tggagaagga gaagctggag caaaacccgg aggagtccca ggacatcaaa    420
gctctgcaga aagaactcga gcaatttgcc aagctcctga agcagaagag gatcaccctg    480
ggatatacac aggccgatgt ggggctcacc ctggggggttc tatttgggaa ggtattcagc    540
caaacgacca tctgccgctt tgaggctctg cagcttagct tcaagaacat gtgtaagctg    600
cggcccttgc tgcagaagtg ggtggaggaa gctgacaaca tgaaaatct tcaggagata    660 tgcaaagcag aaaccctcgt gcaggcccga aagagaaagc gaaccagtat cgagaaccga    720
gtgagaggca acctggagaa tttgttcctg cagtgcccga acccacact gcagcagatc    780 agccacatcg cccagcagct ggggctcgag aaggatgtgg tccgagtgtg gttctgtaac    840
cggcgccaga agggcaagcg atcaagcagc gactatgcac aacgagagga ttttgaggct    900
gctgggtctc ctttctcagg gggaccagtg tcctttcctc tggccccagg gccccatttt    960
ggtaccccag gctatgggag ccctcacttc actgcactgt actcctcggt cccttttccct   1020 gaggggggaag cctttccccc tgtctccgtc accactctgg gctctcccat gcattcaaac   1080
tga                                                                   1083

<210> SEQ ID NO 7
<211> LENGTH: 92
<212> TYPE: DNA
<213> ORGANISM: Artificial Sequence
<220> FEATURE:
<223> OTHER INFORMATION: NANOG F3 primer

<400> SEQUENCE: 7
atgcattcaa actgagctac taacttcagc ctgctgaagc aggctggaga cgtggaggag     60
aaccctggac ctatgagtgt ggatccagct tg                                   92

<210> SEQ ID NO 8
<211> LENGTH: 35
<212> TYPE: DNA
<213> ORGANISM: Artificial Sequence
<220> FEATURE:
<223> OTHER INFORMATION: NANOG R3 primer

<400> SEQUENCE: 8
tgcaataaac aagtttcaca cgtcttcagg ttgca                                35

<210> SEQ ID NO 9
<211> LENGTH: 1005
<212> TYPE: DNA
<213> ORGANISM: Artificial Sequence
<220> FEATURE:
<223> OTHER INFORMATION: NANOG amplicon

<400> SEQUENCE: 9
atgcattcaa actgagctac taacttcagc ctgctgaagc aggctggaga cgtggaggag     60
aaccctggac ctatgagtgt ggatccagct tgtccccaaa gcttgccttg ctttgaagca    120
tccgactgta aagaatcttc acctatgcct gtgatttgtg ggcctgaaga aaactatcca    180
tccttgcaaa tgtcttctgc tgagatgcct cacacggaga ctgtctctcc tcttccttcc    240
tccatggatc tgcttattca ggacagccct gattcttcca ccagtcccaa aggcaaacaa    300
cccacttctg cagagaagag tgtcgcaaaa aaggaagaca aggtcccggt caagaaacag    360
aagaccagaa ctgtgttctc ttccacccag ctgtgtgtac tcaatgatag atttcagaga    420
cagaaatacc tcagcctcca gcagatgcaa gaactctcca acatcctgaa cctcagctac    480
```

| | | | | |
|---|---|---|---|---|
| aaacaggtga | agacctggtt | ccagaaccag | agaatgaaat | ctaagaggtg | gcagaaaaac | 540 |
| aactggccga | agaatagcaa | tggtgtgacg | cagaaggcct | cagcacctac | ctaccccagc | 600 |
| ctttactctt | cctaccacca | gggatgcctg | gtgaacccga | ctgggaacct | tccaatgtgg | 660 |
| agcaaccaga | cctggaacaa | ttcaacctgg | agcaaccaga | cccagaacat | ccagtcctgg | 720 |
| agcaaccact | cctggaacac | tcagacctgg | tgcacccaat | cctggaacaa | tcaggcctgg | 780 |
| aacagtccct | tctataactg | tggagaggaa | tctctgcagt | cctgcatgca | gttccagcca | 840 |
| aattctcctg | ccagtgactt | ggaggctgcc | ttggaagctg | ctggggaagg | ccttaatgta | 900 |
| atacagcaga | ccactaggta | ttttagtact | ccacaaacca | tggatttatt | cctaaactac | 960 |
| tccatgaaca | tgcaacctga | agacgtgtga | aacttgttta | ttgca | | 1005 |

<210> SEQ ID NO 10
<211> LENGTH: 20
<212> TYPE: DNA
<213> ORGANISM: Artificial Sequence
<220> FEATURE:
<223> OTHER INFORMATION: pcDNA3.1 F4 primer

<400> SEQUENCE: 10
aacttgttta ttgcagctta                                         20

<210> SEQ ID NO 11
<211> LENGTH: 20
<212> TYPE: DNA
<213> ORGANISM: Artificial Sequence
<220> FEATURE:
<223> OTHER INFORMATION: pcDNA3.1 R4 primer

<400> SEQUENCE: 11
tatagtgagt cgtattaatt                                         20

<210> SEQ ID NO 12
<211> LENGTH: 3204
<212> TYPE: DNA
<213> ORGANISM: Artificial Sequence
<220> FEATURE:
<223> OTHER INFORMATION: pcDNA3.1 amplicon

<400> SEQUENCE: 12

| | | | | |
|---|---|---|---|---|
| aacttgttta | ttgcagctta | taatggttac | aaataaagca | atagcatcac | aaatttcaca | 60 |
| aataaagcat | ttttttcact | gcattctagt | tgtggtttgt | ccaaactcat | caatgtatct | 120 |
| tatcatgtct | gtataccgtc | gacctctagc | tagagcttgg | cgtaatcatg | gtcatagctg | 180 |
| tttcctgtgt | gaaattgtta | tccgctcaca | attccacaca | acatacgagc | cggaagcata | 240 |
| aagtgtaaag | cctggggtgc | ctaatgagtg | agctaactca | cattaattgc | gttgcgctca | 300 |
| ctgcccgctt | tccagtcggg | aaacctgtcg | tgccagctgc | attaatgaat | cggccaacgc | 360 |
| gcggggagag | gcggtttgcg | tattgggcgc | tcttccgctt | cctcgctcac | tgactcgctg | 420 |
| cgctcggtcg | ttcggctgcg | gcgagcggta | tcagctcact | caaaggcggt | aatacggtta | 480 |
| tccacagaat | caggggataa | cgcaggaaag | aacatgtgag | caaaaggcca | gcaaaaggcc | 540 |
| aggaaccgta | aaaaggccgc | gttgctggcg | ttttttccata | ggctccgccc | ccctgacgag | 600 |
| catcacaaaa | atcgacgctc | aagtcagagg | tggcgaaacc | cgacaggact | ataaagatac | 660 |
| caggcgtttc | ccctggaag | ctccctcgtg | cgctctcctg | ttccgaccct | gccgcttacc | 720 |
| ggatacctgt | ccgcctttct | cccttcggga | agcgtggcgc | tttctcatag | ctcacgctgt | 780 |
| aggtatctca | gttcggtgta | ggtcgttcgc | tccaagctgg | gctgtgtgca | cgaaccccc | 840 |

```
gttcagcccg accgctgcgc cttatccggt aactatcgtc ttgagtccaa cccggtaaga    900
cacgacttat cgccactggc agcagccact ggtaacagga ttagcagagc gaggtatgta    960
ggcggtgcta cagagttctt gaagtggtgg cctaactacg gctacactag aagaacagta   1020
tttggtatct gcgctctgct gaagccagtt accttcggaa aaagagttgg tagctcttga   1080
tccggcaaac aaaccaccgc tggtagcggt ttttttgttt gcaagcagca gattacgcgc   1140
agaaaaaaag gatctcaaga agatcctttg atcttttcta cggggtctga cgctcagtgg   1200
aacgaaaact cacgttaagg gattttggtc atgagattat caaaaaggat cttcacctag   1260
atccttttaa attaaaaatg aagttttaaa tcaatctaaa gtatatatga gtaaacttgg   1320
tctgacagtt accaatgctt aatcagtgag gcacctatct cagcgatctg tctatttcgt   1380
tcatccatag ttgcctgact ccccgtcgtg tagataacta cgatacggga gggcttacca   1440
tctggcccca gtgctgcaat gataccgcga gacccacgct caccggctcc agatttatca   1500
gcaataaacc agccagccgg aagggccgag cgcagaagtg gtcctgcaac tttatccgcc   1560
tccatccagt ctattaattg ttgccgggaa gctagagtaa gtagttcgcc agttaatagt   1620
ttgcgcaacg ttgttgccat tgctacaggc atcgtggtgt cacgctcgtc gtttggtatg   1680
gcttcattca gctccggttc ccaacgatca aggcgagtta catgatcccc catgttgtgc   1740
aaaaaagcgg ttagctcctt cggtcctccg atcgttgtca gaagtaagtt ggccgcagtg   1800
ttatcactca tggttatggc agcactgcat aattctctta ctgtcatgcc atccgtaaga   1860
tgcttttctg tgactggtga gtactcaacc aagtcattct gagaatagtg tatgcggcga   1920
ccgagttgct cttgcccggc gtcaatacgg gataataccg cgccacatag cagaacttta   1980
aaagtgctca tcattggaaa acgttcttcg gggcgaaaac tctcaaggat cttaccgctg   2040
ttgagatcca gttcgatgta acccactcgt gcacccaact gatcttcagc atcttttact   2100
ttcaccagcg tttctgggtg agcaaaaaca ggaaggcaaa atgccgcaaa aaagggaata   2160
agggcgacac ggaaatgttg aatactcata ctcttccttt ttcaatatta ttgaagcatt   2220
tatcagggtt attgtctcat gagcggatac atatttgaat gtatttagaa aaataaacaa   2280
ataggggttc cgcgcacatt tccccgaaaa gtgccacctg acgtcgacgg atcgggagat   2340
ctcccgatcc cctatggtgc actctcagta caatctgctc tgatgccgca tagttaagcc   2400
agtatctgct ccctgcttgt gtgttggagg tcgctgagta gtgcgcgagc aaaatttaag   2460
ctacaacaag gcaaggcttg accgacaatt gcatgaagaa tctgcttagg gttaggcgtt   2520
ttgcgctgct tcgcgatgta cgggccagat atacgcgttg acattgatta ttgactagtt   2580
attaatagta atcaattacg ggtcattag ttcatagccc atatatggag ttccgcgtta   2640
cataacttac ggtaaatggc ccgcctggct gaccgcccaa cgacccccgc ccattgacgt   2700
caataatgac gtatgttccc atagtaacgc caatagggac tttccattga cgtcaatggg   2760
tggagtattt acggtaaact gcccacttgg cagtacatca agtgtatcat atgccaagta   2820
cgccccctat tgacgtcaat gacggtaaat ggcccgcctg gcattatgcc cagtacatga   2880
ccttatggga ctttcctact tggcagtaca tctacgtatt agtcatcgct attaccatgg   2940
tgatgcggtt ttggcagtac atcaatgggc gtggatagcg gtttgactca cggggatttc   3000
caagtctcca ccccattgac gtcaatggga gtttgttttg gcaccaaaat caacgggact   3060
ttccaaaatg tcgtaacaac tccgccccat tgacgcaaat gggcggtagg cgtgtacggt   3120
gggaggtcta tataagcaga gctctctggc taactagaga acccactgct tactggctta   3180
```

```
tcgaaattaa tacgactcac tata                                              3204

<210> SEQ ID NO 13
<211> LENGTH: 6424
<212> TYPE: DNA
<213> ORGANISM: Artificial Sequence
<220> FEATURE:
<223> OTHER INFORMATION: pcDNA3.1-EF-OCT4-NANOG

<400> SEQUENCE: 13
gacggatcgg gagatctccc gatcccctat ggtgcactct cagtacaatc tgctctgatg    60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggag tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aaatgtcgta acaactccgc cccattgacg caaatgggcg   780
gtaggcgtgt acggtgggag gtctatataa gcagagctct ctggctaact agagaaccca   840
ctgcttactg gcttatcgaa attaatacga ctcactatag gctccggtgc ccgtcagtgg   900
gcagagcgca catcgcccac agtccccgag aagttggggg gaggggtcgg caattgaacc   960
ggtgcctaga gaaggtggcg cggggtaaac tgggaaagtg atgtcgtgta ctggctccgc  1020
cttttttccg agggtggggg agaaccgtat ataagtgcag tagtcgccgt gaacgttctt  1080
tttcgcaacg ggtttgccgc cagaacacag gtaagtgccg tgtgtggttc ccgcgggcct  1140
ggcctcttta cgggttatgg cccttgcgtg ccttgaatta cttccacctg gctccagtac  1200
gtgattcttg atcccgagct ggagccaggg gcgggccttg cgctttagga gccccttcgc  1260
ctcgtgcttg agttgaggcc tggcctgggc gctggggccg ccgcgtgcga atctggtggc  1320
accttcgcgc ctgtctcgct gctttcgata agtctctagc catttaaaat ttttgatgac  1380
ctgctgcgac gcttttttc tggcaagata gtcttgtaaa tgcgggccag gatctgcaca  1440
ctggtatttc ggttttgggg cccgcggccg cgacggggc ccgtgcgtcc cagcgcacat  1500
gttcggcgag gcggggcctg cgagcgcggc caccgagaat cggacggggg tagtctcaag  1560
ctggccggcc tgctctggtg cctggcctcg cgccgccgtg tatcgccccg ccctgggcgg  1620
caaggctggc ccggtcggca ccagttgcgt gagcggaaag atggccgctt ccggccctg   1680
ctccaggggg ctcaaaatgg aggacgcggc gctcgggaga gcgggcgggt gagtcaccca  1740
cacaaaggaa aagggccttt ccgtcctcag ccgtcgcttc atgtgactcc acggagtacc  1800
gggcgccgtc caggcacctc gattagttct ggagcttttg gagtacgtcg tctttaggtt  1860
gggggagggg gttttatgcg atggagtttc cccacactga gtggtggag actgaagtta  1920
ggccagcttg gcacttgatg taattctcgt tggaatttgc ccttttttgag tttggatctt  1980
ggttcattct caagcctcag acagtggttc aaagtttttt tcttccattt caggtgtcgt  2040
```

```
gatggcggga  cacctggctt  cggatttcgc  cttctcgccc  cctccaggtg  gtggaggtga   2100
tgggccaggg  gggccggagc  cgggctgggt  tgatcctcgg  acctggctaa  gcttccaagg   2160
ccctcctgga  gggccaggaa  tcgggccggg  ggttgggcca  ggctctgagg  tgtggggat    2220 tcccccatgc  cccccgccgt  atgagttctg  tgggggatg   gcgtactgtg  ggcccaggt    2280 tggagtgggg  ctagtgcccc  aaggcggctt  ggagacctct  cagcctgagg  gcgaagcagg   2340
agtcggggtg  gagagcaact  ccgatggggc  ctccccggag  ccctgcaccg  tcaccctgg    2400 tgccgtgaag  ctgagaagg   agaagctgga  gcaaaacccg  gaggagtccc  aggacatcaa   2460
agctctgcag  aaagaactcg  agcaatttgc  caagctcctg  aagcagaaga  ggatcaccct   2520
gggatataca  caggccgatg  tggggctcac  cctgggggtt  ctatttggga  aggtattcag   2580
ccaaacgacc  atctgccgct  ttgaggctct  gcagcttagc  ttcaagaaca  tgtgtaagct   2640
gcggcccttg  ctgcagaagt  gggtggagga  agctgacaac  aatgaaaatc  ttcaggagat   2700
atgcaaagca  gaaaccctcg  tgcaggcccg  aaagagaaag  cgaaccagta  tcgagaaccg   2760
agtgagaggc  aacctggaga  atttgttcct  gcagtgcccg  aaacccacac  tgcagcagat   2820
cagccacatc  gcccagcagc  ttgggctcga  aaggatgtg   gtccgagtgt  ggttctgtaa   2880
ccggcgccag  aagggcaagc  gatcaagcag  cgactatgca  caacgagagg  attttgaggc   2940
tgctgggtct  cctttctcag  ggggaccagt  gtccttccct  ctggcccag   ggccccattt   3000 tggtaccccca ggctatggga  gccctcactt  cactgcactg  tactcctcgg  tcccttttccc  3060 tgaggggaa   gcctttcccc  ctgtctccgt  caccactctg  ggctctccca  tgcattcaaa   3120
ctgagctact  aacttcagcc  tgctgaagca  ggctggagac  gtggaggaga  accctggacc   3180
tatgagtgtg  gatccagctt  gtccccaaag  cttgccttgc  tttgaagcat  ccgactgtaa   3240
agaatcttca  cctatgcctg  tgatttgtgg  gcctgaagaa  aactatccat  ccttgcaaat   3300
gtcttctgct  gagatgcctc  acacggagac  tgtctctcct  cttccttcct  ccatggatct   3360
gcttattcag  gacagccctg  attcttccac  cagtcccaaa  ggcaaacaac  ccacttctgc   3420
agagaagagt  gtcgcaaaaa  aggaagacaa  ggtcccggtc  aagaaacaga  agaccagaac   3480
tgtgttctct  tccacccagc  tgtgtgtact  caatgataga  tttcagagac  agaaatacct   3540
cagcctccag  cagatgcaag  aactctccaa  catcctgaac  ctcagctaca  aacaggtgaa   3600
gacctggttc  cagaaccaga  gaatgaaatc  taagaggtgg  cagaaaaaca  actggccgaa   3660
gaatagcaat  ggtgtgacgc  agaaggcctc  agcacctacc  taccccagcc  tttactcttc   3720
ctaccaccag  ggatgcctgg  tgaacccgac  tgggaacctt  ccaatgtgga  gcaaccagac   3780
ctggaacaat  tcaacctgga  gcaaccagac  ccagaacatc  cagtcctgga  gcaaccactc   3840
ctggaacact  cagacctggt  gcacccaatc  ctggaacaat  caggcctgga  acagtccctt   3900
ctataactgt  ggagaggaat  ctctgcagtc  ctgcatgcag  ttccagccaa  attctcctgc   3960
cagtgacttg  gaggctgcct  tggaagctgc  tgggaaggc   cttaatgtaa  tacagcagac   4020
cactaggtat  tttagtactc  cacaaaccat  ggatttattc  ctaaactact  ccatgaacat   4080
gcaacctgaa  gacgtgtgaa  acttgtttat  tgcagcttat  aatggttaca  aataaagcaa   4140
tagcatcaca  aatttcacaa  ataaagcatt  ttttcactg   cattctagtt  gtggtttgtc   4200
caaactcatc  aatgtatctt  atcatgtctg  tataccgtcg  acctctagct  agagcttggc   4260
gtaatcatgg  tcatagctgt  ttcctgtgtg  aaattgttat  ccgctcacaa  ttccacacaa   4320
catacgagcc  ggaagcataa  agtgtaaagc  ctggggtgcc  taatgagtga  gctaactcac   4380
```

| | |
|---|---|
| attaattgcg ttgcgctcac tgcccgcttt ccagtcggga aacctgtcgt gccagctgca | 4440 |
| ttaatgaatc ggccaacgcg cggggagagg cggtttgcgt attgggcgct cttccgcttc | 4500 |
| ctcgctcact gactcgctgc gctcggtcgt tcggctgcgg cgagcggtat cagctcactc | 4560 |
| aaaggcggta atacggttat ccacagaatc aggggataac gcaggaaaga acatgtgagc | 4620 |
| aaaaggccag caaaaggcca ggaaccgtaa aaaggccgcg ttgctggcgt ttttccatag | 4680 |
| gctccgcccc cctgacgagc atcacaaaaa tcgacgctca agtcagaggt ggcgaaaccc | 4740 |
| gacaggacta taaagatacc aggcgtttcc ccctggaagc tccctcgtgc gctctcctgt | 4800 |
| tccgaccctg ccgcttaccg gatacctgtc cgcctttctc ccttcgggaa gcgtggcgct | 4860 |
| ttctcatagc tcacgctgta ggtatctcag ttcggtgtag tcgttcgct ccaagctggg | 4920 |
| ctgtgtgcac gaaccccccg ttcagcccga ccgctgcgcc ttatccggta actatcgtct | 4980 |
| tgagtccaac ccggtaagac acgacttatc gccactggca gcagccactg gtaacaggat | 5040 |
| tagcagagcg aggtatgtag gcggtgctac agagttcttg aagtggtggc ctaactacgg | 5100 |
| ctacactaga agaacagtat ttggtatctg cgctctgctg aagccagtta ccttcggaaa | 5160 |
| aagagttggt agctcttgat ccggcaaaca accaccgct ggtagcggtt ttttttgtttg | 5220 |
| caagcagcag attacgcgca gaaaaaaagg atctcaagaa gatcctttga tcttttctac | 5280 |
| ggggtctgac gctcagtgga acgaaaactc acgttaaggg attttggtca tgagattatc | 5340 |
| aaaaaggatc ttcacctaga tccttttaaa ttaaaaatga agttttaaat caatctaaag | 5400 |
| tatatatgag taaacttggt ctgacagtta ccaatgctta atcagtgagg cacctatctc | 5460 |
| agcgatctgt ctatttcgtt catccatagt tgcctgactc ccgtcgtgt agataactac | 5520 |
| gatacgggag ggcttaccat ctggccccag tgctgcaatg ataccgcgag acccacgctc | 5580 |
| accggctcca gatttatcag caataaacca gccagccgga agggccgagc gcagaagtgg | 5640 |
| tcctgcaact ttatccgcct ccatccagtc tattaattgt tgccgggaag ctagagtaag | 5700 |
| tagttcgcca gttaatagtt tgcgcaacgt tgttgccatt gctacaggca tcgtggtgtc | 5760 |
| acgctcgtcg tttggtatgg cttcattcag ctccggttcc caacgatcaa ggcgagttac | 5820 |
| atgatccccc atgttgtgca aaaaagcggt tagctccttc ggtcctccga tcgttgtcag | 5880 |
| aagtaagttg gccgcagtgt tatcactcat ggttatggca gcactgcata attctcttac | 5940 |
| tgtcatgcca tccgtaagat gcttttctgt gactggtgag tactcaacca agtcattctg | 6000 |
| agaatagtgt atgcggcgac cgagttgctc ttgcccggcg tcaatacggg ataataccgc | 6060 |
| gccacatagc agaactttaa aagtgctcat cattggaaaa cgttcttcgg ggcgaaaact | 6120 |
| ctcaaggatc ttaccgctgt tgagatccag ttcgatgtaa cccactcgtg cacccaactg | 6180 |
| atcttcagca tcttttactt tcaccagcgt ttctgggtga gcaaaaacag gaaggcaaaa | 6240 |
| tgccgcaaaa aagggaataa gggcgacacg gaaatgttga atactcatac tcttcctttt | 6300 |
| tcaatattat tgaagcattt atcagggtta ttgtctcatg agcggataca tatttgaatg | 6360 |
| tatttagaaa aataaacaaa tagggggttcc gcgcacattt ccccgaaaag tgccacctga | 6420 |
| cgtc | 6424 |

<210> SEQ ID NO 14
<211> LENGTH: 92
<212> TYPE: DNA
<213> ORGANISM: Artificial Sequence
<220> FEATURE:
<223> OTHER INFORMATION: NANOG R7 primer

<400> SEQUENCE: 14

```
cccctcgtca gacataggtc cagggttctc ctccacgtct ccagcctgct tcagcaggct    60
gaagttagta gctcacacgt cttcaggttg ca                                  92

<210> SEQ ID NO 15
<211> LENGTH: 1062
<212> TYPE: DNA
<213> ORGANISM: Artificial Sequence
<220> FEATURE:
<223> OTHER INFORMATION: NANOG amplicon

<400> SEQUENCE: 15
atgcattcaa actgagctac taacttcagc ctgctgaagc aggctggaga cgtggaggag    60
aaccctggac ctatgagtgt ggatccagct tgtccccaaa gcttgccttg ctttgaagca   120
tccgactgta aagaatcttc acctatgcct gtgatttgtg ggcctgaaga aaactatcca   180
tccttgcaaa tgtcttctgc tgagatgcct cacacggaga ctgtctctcc tcttccttcc   240
tccatggatc tgcttattca ggacagccct gattcttcca ccagtcccaa aggcaaacaa   300
cccacttctg cagagaagag tgtcgcaaaa aaggaagaca aggtcccggt caagaaacag   360
aagaccagaa ctgtgttctc ttccacccag ctgtgtgtac tcaatgatag atttcagaga   420
cagaaatacc tcagcctcca gcagatgcaa gaactctcca acatcctgaa cctcagctac   480
aaacaggtga agacctggtt ccagaaccag agaatgaaat ctaagaggtg cagaaaaac    540 aactggccga agaatagcaa tggtgtgacg cagaaggcct cagcacctac ctaccccagc   600
ctttactctt cctaccacca gggatgcctg gtgaacccga ctgggaacct tccaatgtgg   660
agcaaccaga cctggaacaa ttcaacctgg agcaaccaga cccagaacat ccagtcctgg   720
agcaaccact cctggaacac tcagacctgg tgcacccaat cctggaacaa tcaggcctgg   780
aacagtccct tctataactg tggagaggaa tctctgcagt cctgcatgca gttccagcca   840
aattctcctg ccagtgactt ggaggctgcc ttggaagctg ctggggaagg ccttaatgta   900
atacagcaga ccactaggta ttttagtact ccacaaacca tggatttatt cctaaactac   960
tccatgaaca tgcaacctga agacgtgtga gctactaact tcagcctgct gaagcaggct  1020
ggagacgtgg aggagaaccc tggacctatg tctgacgagg gg                     1062

<210> SEQ ID NO 16
<211> LENGTH: 38
<212> TYPE: DNA
<213> ORGANISM: Artificial Sequence
<220> FEATURE:
<223> OTHER INFORMATION: EBNA1 F8 primer

<400> SEQUENCE: 16
atgtctgacg aggggccagg tacaggacct ggaaatgg                            38

<210> SEQ ID NO 17
<211> LENGTH: 85
<212> TYPE: DNA
<213> ORGANISM: Artificial Sequence
<220> FEATURE:
<223> OTHER INFORMATION: EBNA1 R8 primer

<400> SEQUENCE: 17
ttatttgtga aatttgtgat gctattgctt tatttgtaac cattataagc tgcaataaac    60
aagtttcact cctgcccttc ctcac                                          85

<210> SEQ ID NO 18
```

<211> LENGTH: 1991
<212> TYPE: DNA
<213> ORGANISM: Artificial Sequence
<220> FEATURE:
<223> OTHER INFORMATION: EBNA1 amplicon

<400> SEQUENCE: 18

```
atgtctgacg aggggccagg tacaggacct ggaaatggcc taggagagaa gggagacaca        60
tctggaccag aaggctccgg cggcagtgga cctcaaagaa gagggggtga taaccatgga       120
cgaggacggg gaagaggacg aggacgagga ggcggaagac caggagcccc gggcggctca       180
ggatcagggc caagacatag agatggtgtc cggagacccc aaaaacgtcc aagttgcatt       240
ggctgcaaag ggacccacgg tggaacagga gcaggagcag gagcgggagg ggcaggagca       300
ggaggggcag gagcaggagg aggggcagga gcaggaggag gggcaggagg ggcaggaggg       360
gcaggagggg caggagcagg aggaggggca ggagcaggag gaggggcagg aggggcagga       420
ggggcaggag caggaggagg ggcaggagca ggaggagggg caggaggggc aggagcagga       480
ggaggggcag gaggggcagg aggggcagga gcaggaggag gggcaggagc aggaggaggg       540
gcaggagggg caggagcagg aggaggggca gaggggcagg aggggcagg agcaggagga       600
ggggcaggag caggaggggc aggaggggca ggaggggcag gagcaggagg ggcaggagca       660
ggaggagggg caggaggggc aggaggggca ggagcaggag gggcaggagc aggaggggca       720
ggagcaggag gggcaggagc aggaggggca ggaggggcag gagcaggagg ggcaggaggg       780
gcaggagcag gaggggcagg aggggcagga gcaggaggag gggcaggagg gcaggagca       840
ggaggagggg caggaggggc aggagcagga ggggcaggag gggcaggagc aggaggggca       900
ggaggggcag gagcaggagg ggcaggaggg gcaggagcag gaggagggc aggagcagga       960
ggggcaggag caggaggtgg aggccggggt cgaggaggca gtggaggccg gggtcgagga      1020
ggtagtggag gccgggggtcg aggaggtagt ggaggccgcc ggggtagagg acgtgaaaga      1080
gccaggggg gaagtcgtga aagagccagg gggagaggtc gtggacgtgg agaaaagagg      1140
cccaggagtc ccagtagtca gtcatcatca tccgggtctc caccgcgcag gccccctcca      1200
ggtagaaggc cattttttcca ccctgtaggg aagccgatt attttgaata ccaccaagaa      1260
ggtggcccag atggtgagcc tgacgtgccc ccgggagcga tagagcaggg ccccgcagat      1320
gacccaggag aaggcccaag cactggaccc cggggtcagg gtgatggagg caggcgcaaa      1380
aaaggagggt ggtttggaaa gcatcgtggt caaggaggtt ccaacccgaa atttgagaac      1440
attgcagaag gtttaagagc tctcctggct aggagtcacg tagaaaggac taccgacgaa      1500
ggaacttggg tcgccggtgt gttcgtatat ggaggtagta agacctccct ttacaaccta      1560
aggcgaggaa ctgcccttgc tattccacaa tgtcgtctta ccattgag tcgtctcccc      1620
tttggaatgg cccctggacc cggcccacaa cctggcccgc taaggagtc cattgtctgt      1680
tatttcatgg tcttttaca aactcatata tttgctgagg ttttgaagga tgcgattaag      1740
gaccttgtta tgacaaagcc cgctcctacc tgcaatatca gggtgactgt gtgcagcttt      1800
gacgatggag tagatttgcc tccctggttt ccacctatgg tggaagggc tgccgcggag      1860
ggtgatgacg gagatgacgg agatgaagga ggtgatggag atgagggtga ggaagggcag      1920
gagtgaaact tgtttattgc agcttataat ggttacaaat aaagcaatag catcacaaat      1980
ttcacaaata a                                                            1991
```

<210> SEQ ID NO 19
<211> LENGTH: 101

```
<212> TYPE: DNA
<213> ORGANISM: Artificial Sequence
<220> FEATURE:
<223> OTHER INFORMATION: OriP F9 primer

<400> SEQUENCE: 19
aaatttcaca aataaagcat ttttttcact gcattctagt tgtggtttgt ccaaactcat    60
caatgtatct tatcatgtct gaacgggtag catatgcttc c                       101

<210> SEQ ID NO 20
<211> LENGTH: 34
<212> TYPE: DNA
<213> ORGANISM: Artificial Sequence
<220> FEATURE:
<223> OTHER INFORMATION: OriP R9 primer

<400> SEQUENCE: 20
gaggtcgacg gtataaggaa aaggacaagc agcg                                34

<210> SEQ ID NO 21
<211> LENGTH: 1885
<212> TYPE: DNA
<213> ORGANISM: Artificial Sequence
<220> FEATURE:
<223> OTHER INFORMATION: OriP amplicon

<400> SEQUENCE: 21
aaatttcaca aataaagcat ttttttcact gcattctagt tgtggtttgt ccaaactcat    60
caatgtatct tatcatgtct gaacgggtag catatgcttc ccgggtagta gtatatacta   120
tccagactaa ccctaattca atagcatatg ttacccaacg ggaagcatat gctatcgaat   180
tagggttagt aaaagggtcc taaggaacag cgatatctcc cacccatga gctgtcacgg   240 ttttatttac atggggtcag gattccacga gggtagtgaa ccattttagt cacaagggca   300
gtggctgaag atcaaggagc gggcagtgaa ctctcctgaa tcttcgcctg cttcttcatt   360
ctccttcgtt tagctaatag aataactgct gagttgtgaa cagtaaggtg tatgtgaggt   420
gctcgaaaac aaggtttcag gtgacgcccc cagaataaaa tttggacggg gggttcagtg   480
gtggcattgt gctatgacac caatataacc ctcacaaacc ccttgggcaa taaatactag   540
tgtaggaatg aaacattctg aatatcttta acaatagaaa tccatggggt ggggacaagc   600
cgtaaagact ggatgtccat ctcacacgaa tttatgcta tgggcaacac ataatcctag   660
tgcaatatga tactggggtt attaagatgt gtcccaggca gggaccaaga caggtgaacc   720
atgttgttac actctatttg taacaagggg aaagagagtg gacgccgaca gcagcggact   780
ccactggttg tctctaacac ccccgaaaat taaacgggc tccacgccaa tggggcccat   840
aaacaaagac aagtggccac tcttttttttt gaaattgtgg agtgggggca cgcgtcagcc   900
cccacacgcc gccctgcggt tttggactgt aaaataaggg tgtaataact tggctgattg   960 taacccgct aaccactgcg gtcaaaccac ttgcccacaa aaccactaat ggcacccgg    1020 ggaatacctg cataagtagg tgggcgggcc aagatagggg cgcgattgct gcgatctgga   1080
ggacaaatta cacacacttg cgcctgagcg ccaagcacag ggttgttggt cctcatattc   1140
acgaggtcgc tgagagcacg gtgggctaat gttgccatgg gtagcatata ctacccaaat   1200
atctggatag catatgctat cctaatctat atctgggtag cataggctat cctaatctat   1260
atctgggtag catatgctat cctaatctat atctgggtag tatatgctat cctaatttat   1320
atctgggtag cataggctat cctaatctat atctgggtag catatgctat cctaatctat   1380
```

-continued

```
atctgggtag tatatgctat cctaatctgt atccgggtag catatgctat cctaatagag    1440
attagggtag tatatgctat cctaatttat atctgggtag catatactac ccaaatatct    1500
ggatagcata tgctatccta atctatatct gggtagcata tgctatccta atctatatct    1560
gggtagcata ggctatccta atctatatct gggtagcata tgctatccta atctatatct    1620
gggtagtata tgctatccta atttatatct gggtagcata ggctatccta atctatatct    1680
gggtagcata tgctatccta atctatatct gggtagtata tgctatccta atctgtatcc    1740
gggtagcata tgctatcctc atgcatatac agtcagcata tgatacccag tagtagagtg    1800
ggagtgctat cctttgcata tgccgccacc tcccaagggg gcgtgaattt tcgctgcttg    1860 tcctttttcct tataccgtcg acctc                                         1885
```

<210> SEQ ID NO 22
<211> LENGTH: 20
<212> TYPE: DNA
<213> ORGANISM: Artificial Sequence
<220> FEATURE:
<223> OTHER INFORMATION: pcDNA3.1 F10 primer

<400> SEQUENCE: 22

```
tataccgtcg acctctagct                                                  20
```

<210> SEQ ID NO 23
<211> LENGTH: 3073
<212> TYPE: DNA
<213> ORGANISM: Artificial Sequence
<220> FEATURE:
<223> OTHER INFORMATION: pcDNA3.1 amplicon

<400> SEQUENCE: 23

```
tataccgtcg acctctagct agagcttggc gtaatcatgg tcatagctgt ttcctgtgtg      60
aaattgttat ccgctcacaa ttccacacaa catacgagcc ggaagcataa agtgtaaagc     120
ctggggtgcc taatgagtga gctaactcac attaattgcg ttgcgctcac tgcccgcttt     180
ccagtcggga aacctgtcgt gccagctgca ttaatgaatc ggccaacgcg cggggagagg     240
cggtttgcgt attgggcgct cttccgcttc ctcgctcact gactcgctgc gctcggtcgt     300
tcggctgcgg cgagcggtat cagctcactc aaaggcggta atacggttat ccacagaatc     360
aggggataac gcaggaaaga acatgtgagc aaaaggccag caaaaggcca ggaaccgtaa     420
aaaggccgcg ttgctggcgt ttttccatag gctccgcccc cctgacgagc atcacaaaaa     480
tcgacgctca gtcagaggt ggcgaaaccc gacaggacta taaagatacc aggcgtttcc     540
ccctggaagc tccctcgtgc gctctcctgt tccgaccctg ccgcttaccg gatacctgtc     600
cgcctttctc ccttcgggaa gcgtggcgct ttctcatagc tcacgctgta ggtatctcag     660
ttcggtgtag gtcgttcgct ccaagctggg ctgtgtgcac gaaccccccg ttcagcccga     720
ccgctgcgcc ttatccggta actatcgtct tgagtccaac ccggtaagac acgacttatc     780
gccactggca gcagccactg gtaacaggat tagcagagcg aggtatgtag gcggtgctac     840
agagttcttg aagtggtggc ctaactacgg ctacactaga agaacagtat ttggtatctg     900
cgctctgctg aagccagtta ccttcggaaa aagagttggt agctcttgat ccggcaaaca     960
aaccaccgct ggtagcggtt ttttgtttg caagcagcag attacgcgca gaaaaaaagg    1020
atctcaagaa gatcctttga tcttttctac ggggtctgac gctcagtgga acgaaaactc    1080
acgttaaggg attttggtca tgagattatc aaaaaggatc ttcacctaga tccttttaaa    1140
ttaaaaatga agttttaaat caatctaaag tatatatgag taaacttggt ctgacagtta    1200
```

| | |
|---|---|
| ccaatgctta atcagtgagg cacctatctc agcgatctgt ctatttcgtt catccatagt | 1260 |
| tgcctgactc cccgtcgtgt agataactac gatacgggag ggcttaccat ctggccccag | 1320 |
| tgctgcaatg ataccgcgag acccacgctc accggctcca gatttatcag caataaacca | 1380 |
| gccagccgga agggccgagc gcagaagtgg tcctgcaact ttatccgcct ccatccagtc | 1440 |
| tattaattgt tgccgggaag ctagagtaag tagttcgcca gttaatagtt tgcgcaacgt | 1500 |
| tgttgccatt gctacaggca tcgtggtgtc acgctcgtcg tttggtatgg cttcattcag | 1560 |
| ctccggttcc caacgatcaa ggcgagttac atgatccccc atgttgtgca aaaaagcggt | 1620 |
| tagctccttc ggtcctccga tcgttgtcag aagtaagttg gccgcagtgt tatcactcat | 1680 |
| ggttatggca gcactgcata attctcttac tgtcatgcca tccgtaagat gcttttctgt | 1740 |
| gactggtgag tactcaacca agtcattctg agaatagtgt atgcggcgac cgagttgctc | 1800 |
| ttgcccggcg tcaatacggg ataataccgc gccacatagc agaactttaa aagtgctcat | 1860 |
| cattggaaaa cgttcttcgg ggcgaaaact ctcaaggatc ttaccgctgt tgagatccag | 1920 |
| ttcgatgtaa cccactcgtg cacccaactg atcttcagca tcttttactt tcaccagcgt | 1980 |
| ttctgggtga gcaaaaacag gaaggcaaaa tgccgcaaaa aagggaataa gggcgacacg | 2040 |
| gaaatgttga atactcatac tcttcctttt tcaatattat tgaagcattt atcagggtta | 2100 |
| ttgtctcatg agcggataca tatttgaatg tatttagaaa aataaacaaa taggggttcc | 2160 |
| gcgcacattt ccccgaaaag tgccacctga cgtcgacgga tcgggagatc tcccgatccc | 2220 |
| ctatggtgca ctctcagtac aatctgctct gatgccgcat agttaagcca gtatctgctc | 2280 |
| cctgcttgtg tgttggaggt cgctgagtag tgcgcgagca aaatttaagc tacaacaagg | 2340 |
| caaggcttga ccgacaattg catgaagaat ctgcttaggg ttaggcgttt tgcgctgctt | 2400 |
| cgcgatgtac gggccagata tacgcgttga cattgattat tgactagtta ttaatagtaa | 2460 |
| tcaattacgg ggtcattagt tcatagccca tatatggagt tccgcgttac ataacttacg | 2520 |
| gtaaatggcc cgcctggctg accgcccaac gacccccgcc cattgacgtc aataatgacg | 2580 |
| tatgttccca tagtaacgcc aatagggact ttccattgac gtcaatgggt ggagtattta | 2640 |
| cggtaaactg cccacttggc agtacatcaa gtgtatcata tgccaagtac gccccctatt | 2700 |
| gacgtcaatg acggtaaatg gcccgcctgg cattatgccc agtacatgac cttatgggac | 2760 |
| tttcctactt ggcagtacat ctacgtatta gtcatcgcta ttaccatggt gatgcggttt | 2820 |
| tggcagtaca tcaatgggcg tggatagcgg tttgactcac ggggatttcc aagtctccac | 2880 |
| cccattgacg tcaatgggag tttgttttgg caccaaaatc aacgggactt tccaaaatgt | 2940 |
| cgtaacaact ccgccccatt gacgcaaatg ggcggtaggc gtgtacggtg ggaggtctat | 3000 |
| ataagcagag ctctctggct aactagagaa cccactgctt actggcttat cgaaattaat | 3060 |
| acgactcact ata | 3073 |

```
<210> SEQ ID NO 24
<211> LENGTH: 10196
<212> TYPE: DNA
<213> ORGANISM: Artificial Sequence
<220> FEATURE:
<223> OTHER INFORMATION: pcDNA3.1-EF-OCT4-NANOG-EBNA1-OriP

<400> SEQUENCE: 24
```

| | |
|---|---|
| gacggatcgg gagatctccc gatccctat ggtgcactct cagtacaatc tgctctgatg | 60 |
| ccgcatagtt aagccagtat ctgctccctg cttgtgtgtt ggaggtcgct gagtagtgcg | 120 |

```
cgagcaaaat ttaagctaca acaaggcaag gcttgaccga caattgcatg aagaatctgc      180
ttagggttag gcgttttgcg ctgcttcgcg atgtacgggc cagatatacg cgttgacatt      240
gattattgac tagttattaa tagtaatcaa ttacggggtc attagttcat agcccatata      300
tggagttccg cgttacataa cttacggtaa atggcccgcc tggctgaccg cccaacgacc      360
cccgcccatt gacgtcaata atgacgtatg ttcccatagt aacgccaata gggactttcc      420
attgacgtca atgggtggag tatttacggt aaactgccca cttggcagta catcaagtgt      480
atcatatgcc aagtacgccc cctattgacg tcaatgacgg taaatggccc gcctggcatt      540
atgcccagta catgacctta tgggactttc ctacttggca gtacatctac gtattagtca      600
tcgctattac catggtgatg cggttttggc agtacatcaa tgggcgtgga tagcggtttg      660
actcacgggg atttccaagt ctccacccca ttgacgtcaa tgggagtttg ttttggcacc      720
aaaatcaacg ggactttcca aaatgtcgta acaactccgc cccattgacg caaatgggcg      780
gtaggcgtgt acggtgggag gtctatataa gcagagctct ctggctaact agagaaccca      840
ctgcttactg gcttatcgaa attaatacga ctcactatag gctccggtgc ccgtcagtgg      900
gcagagcgca catcgcccac agtccccgag aagttggggg gaggggtcgg caattgaacc      960
ggtgcctaga gaaggtggcg cggggtaaac tgggaaagtg atgtcgtgta ctggctccgc     1020
cttttttccg agggtggggg agaaccgtat ataagtgcag tagtcgccgt gaacgttctt     1080
tttcgcaacg ggtttgccgc cagaacacag gtaagtgccg tgtgtggttc ccgcgggcct     1140
ggcctcttta cgggttatgg cccttgcgtg ccttgaatta cttccacctg gctccagtac     1200
gtgattcttg atcccgagct ggagccaggg gcgggccttg cgctttagga gccccttcgc     1260
ctcgtgcttg agttgaggcc tggcctgggc gctggggccg ccgcgtgcga atctggtggc     1320
accttcgcgc ctgtctcgct gctttcgata agtctctagc catttaaaat ttttgatgac     1380
ctgctgcgac gctttttttc tggcaagata gtcttgtaaa tgcgggccag atctgcaca     1440 ctggtatttc ggtttttggg cccgcggccg gcgacgggc ccgtgcgtcc cagcgcacat     1500
gttcggcgag gcggggcctg cgagcgcggc caccgagaat cggacggggg tagtctcaag     1560
ctggccggcc tgctctggtg cctggcctcg cgccgccgtg tatcgccccg ccctgggcgg     1620
caaggctggc ccggtcggca ccagttgcgt gagcggaaag atggccgctt cccggccctg     1680
ctccaggggg ctcaaaatgg aggacgcggc gctcgggaga cgggcgggt gagtcaccca     1740 cacaaaggaa aagggccttt ccgtcctcag ccgtcgcttc atgtgactcc acggagtacc     1800
gggcgccgtc caggcacctc gattagttct ggagcttttg gagtacgtcg tctttaggtt     1860
ggggggaggg gttttatgcg atggagtttc cccacactga gtgggtggag actgaagtta     1920
ggccagcttg gcacttgatg taattctcgt tggaatttgc cctttttgag tttggatctt     1980
ggttcattct caagcctcag acagtggttc aaagtttttt tcttccattt caggtgtcgt     2040
gatgcgggga cacctggctt cggatttcgc cttctcgccc cctccaggtg gtggaggtga     2100
tgggccaggg gggccggagc cgggctgggt tgatcctcgg acctggctaa gcttccaagg     2160
ccctcctgga gggccaggaa tcgggccggg ggttgggcca ggctctgagg tgtggggat     2220 tcccccatgc ccccgccgt atgagttctg tggggatg gcgtactgtg gccccaggt     2280 tggagtgggg ctagtgcccc aaggcggctt ggagacctct cagcctgagg gcgaagcagg     2340
agtcggggtg gagagcaact ccgatgggc ctccccggag ccctgcaccg tcaccctgg     2400 tgccgtgaag ctggagaagg agaagctgga gcaaacccg gaggagtccc aggacatcaa     2460
agctctgcag aaagaactcg agcaatttgc caagctcctg aagcagaaga ggatcaccct     2520
```

```
gggatataca caggccgatg tggggctcac cctgggggtt ctatttggga aggtattcag    2580
ccaaacgacc atctgccgct ttgaggctct gcagcttagc ttcaagaaca tgtgtaagct    2640
gcggcccttg ctgcagaagt gggtggagga agctgacaac aatgaaaatc ttcaggagat    2700
atgcaaagca gaaaccctcg tgcaggcccg aaagagaaag cgaaccagta tcgagaaccg    2760
agtgagaggc aacctggaga atttgttcct gcagtgcccg aaacccacac tgcagcagat    2820
cagccacatc gcccagcagc ttgggctcga aaggatgtg gtccgagtgt ggttctgtaa    2880
ccggcgccag aagggcaagc gatcaagcag cgactatgca caacgagagg attttgaggc    2940
tgctgggtct cctttctcag ggggaccagt gtcctttcct ctggcccag ggccccattt    3000
tggtacccca ggctatggga gccctcactt cactgcactg tactcctcgg tcccttccc    3060
tgaggggaa gcctttcccc ctgtctccgt caccactctg ggctctccca tgcattcaaa    3120
ctgagctact aacttcagcc tgctgaagca ggctggagac gtggaggaga accctggacc    3180
tatgagtgtg gatccagctt gtccccaaag cttgccttgc tttgaagcat ccgactgtaa    3240
agaatcttca cctatgcctg tgatttgtgg gcctgaagaa aactatccat ccttgcaaat    3300
gtcttctgct gagatgcctc acacggagac tgtctctcct cttccttcct ccatggatct    3360
gcttattcag gacagccctg attcttccac cagtcccaaa ggcaaacaac ccacttctgc    3420
agagaagagt gtcgcaaaaa aggaagacaa ggtcccggtc aagaaacaga agaccagaac    3480
tgtgttctct tccacccagc tgtgtgtact caatgataga tttcagagac agaaatacct    3540
cagcctccag cagatgcaag aactctccaa catcctgaac ctcagctaca acaggtgaa    3600
gacctggttc cagaaccaga gaatgaaatc taagaggtgg cagaaaaaca actggccgaa    3660
gaatagcaat ggtgtgacgc agaaggcctc agcacctacc taccccagcc tttactcttc    3720
ctaccaccag ggatgcctgg tgaacccgac tgggaacctt ccaatgtgga gcaaccagac    3780
ctggaacaat tcaacctgga gcaaccagac ccagaacatc cagtcctgga gcaaccactc    3840
ctggaacact cagacctggt gcacccaatc ctggaacaat caggcctgga acagtccctt    3900
ctataactgt ggagaggaat ctctgcagtc ctgcatgcag ttccagccaa attctcctgc    3960
cagtgacttg gaggctgcct tggaagctgc tggggaaggc cttaatgtaa tacagcagac    4020
cactaggtat tttagtactc cacaaaccat ggatttattc ctaaactact ccatgaacat    4080
gcaacctgaa gacgtgtgag ctactaactt cagcctgctg aagcaggctg agacgtgga    4140
ggagaaccct ggacctatgt ctgacgaggg gccaggtaca ggacctggaa atggcctagg    4200
agagaaggga gacacatctg gaccagaagg ctccggcgc agtggacctc aaagaagagg    4260
gggtgataac catggacgag gacggggaag aggacgagga cgaggaggcg aagaccagg    4320
agccccgggc ggctcaggat cagggccaag acatagagat ggtgtccgga gaccccaaaa    4380
acgtccaagt tgcattggct gcaaagggac ccacggtgga acaggagcag gagcaggagc    4440
gggaggggca ggagcaggag gggcaggagc aggaggaggg gcaggagcag gaggagggc    4500
aggaggggca ggaggggcag gaggggcagg agcaggagga gggcaggag caggaggagg    4560
ggcaggaggg gcaggagggg caggagcagg aggagggca ggagcaggag gaggggcagg    4620
aggggcagga gcaggaggag gggcaggagg ggcaggaggg gcaggagcag gaggagggc    4680
aggagcagga gaggggcag gaggggcagg agcaggagga gggcaggag gggcaggagg    4740
ggcaggagca ggaggagggg caggagcagg aggggcagga gggcaggag gggcaggagc    4800
aggaggggca ggagcaggag gagggcagg aggggcagga ggggcaggag caggaggggc    4860
```

```
aggagcagga ggggcaggag caggaggggc aggagcagga ggggcaggag gggcaggagc   4920
aggaggggca ggaggggcag gagcaggagg ggcaggaggg gcaggagcag gaggaggggc   4980
aggaggggca ggagcaggag gaggggcagg aggggcagga gcaggagggg caggaggggc   5040
aggagcagga ggggcaggag gggcaggagc aggaggggca ggaggggcag gagcaggagg   5100
aggggcagga gcaggagggg caggagcagg aggtggaggc cggggtcgag gaggcagtgg   5160 aggccgggt cgaggaggta gtggaggccg gggtcgagga ggtagtggag gccgccgggg   5220
tagaggacgt gaaagagcca ggggggggaag tcgtgaaaga gccaggggga gaggtcgtgg   5280
acgtggagaa aagaggccca ggagtcccag tagtcagtca tcatcatccg ggtctccacc   5340
gcgcaggccc cctccaggta aaggccatt tttccaccct gtaggggaag ccgattattt   5400
tgaataccac caagaaggtg cccagatgg tgagcctgac gtgccccgg gagcgataga   5460 gcagggcccc gcagatgacc caggagaagg cccaagcact ggaccccggg gtcagggtga   5520
tggaggcagg cgcaaaaaag gagggtggtt tggaaagcat cgtggtcaag gaggttccaa   5580
cccgaaattt gagaacattg cagaaggttt aagagctctc ctggctagga gtcacgtaga   5640
aaggactacc gacgaaggaa cttgggtcgc cggtgtgttc gtatatggag gtagtaagac   5700 ctcccttac aacctaaggc gaggaactgc ccttgctatt ccacaatgtc gtcttacacc   5760
attgagtcgt ctcccctttg gaatggcccc tggacccggc ccacaacctg gcccgctaag   5820
ggagtccatt gtctgttatt tcatggtctt tttacaaact catatatttg ctgaggtttt   5880
gaaggatgcg attaaggacc ttgttatgac aaagcccgct cctacctgca atatcagggt   5940
gactgtgtgc agctttgacg atggagtaga tttgcctccc tggtttccac ctatggtgga   6000
aggggctgcc gcggagggtg atgacggaga tgacggagat gaaggaggtg atggagatga   6060
gggtgaggaa gggcaggagt gaaacttgtt tattgcagct tataatggtt acaaataaag   6120
caatagcatc acaaatttca caaataaagc attttttca ctgcattcta gttgtggttt   6180
gtccaaactc atcaatgtat cttatcatgt ctgaacgggt agcatatgct tcccgggtag   6240
tagtatatac tatccagact aaccctaatt caatagcata tgttacccaa cgggaagcat   6300
atgctatcga attagggtta gtaaaagggt cctaaggaac agcgatatct cccacccat   6360 gagctgtcac ggttttattt acatggggtc aggattccac gagggtagtg aaccatttta   6420
gtcacaaggg cagtggctga agatcaagga gcggcagtg aactctcctg aatcttcgcc   6480
tgcttcttca ttctccttcg tttagctaat agaataactg ctgagttgtg aacagtaagg   6540
tgtatgtgag gtgctcgaaa acaaggtttc aggtgacgcc cccagaataa atttggacg   6600 ggggggttcag tggtggcatt gtgctatgac accaatataa ccctcacaaa ccccttgggc   6660
aataaatact agtgtaggaa tgaaacattc tgaatatctt taacaataga aatccatggg   6720
gtggggacaa gccgtaaaga ctggatgtcc atctcacacg aatttatggc tatgggcaac   6780
acataatcct agtgcaatat gatactgggg ttattaagat gtgtcccagg cagggaccaa   6840
gacaggtgaa ccatgttgtt acactctatt tgtaacaagg ggaagagag tggacgccga   6900 cagcagcgga ctccactggt tgtctctaac accccgaaa attaaacggg gctccacgcc   6960 aatgggccc ataaacaaag acaagtggcc actctttttt ttgaaattgt ggagtggggg   7020
cacgcgtcag ccccacacg ccgccctgcg gttttggact gtaaaataag ggtgtaataa   7080
cttggctgat tgtaaccccg ctaaccactg cggtcaaacc acttgcccac aaaaccacta   7140
atggcacccc ggggaatacc tgcataagta ggtgggcggg ccaagatagg ggcgcgattg   7200
ctgcgatctg gaggacaaat tacacacact tgcgcctgag cgccaagcac agggttgttg   7260
```

```
gtcctcatat tcacgaggtc gctgagagca cggtgggcta atgttgccat gggtagcata   7320
tactacccaa atatctggat agcatatgct atcctaatct atatctgggt agcataggct   7380
atcctaatct atatctgggt agcatatgct atcctaatct atatctgggt agtatatgct   7440
atcctaattt atatctgggt agcataggct atcctaatct atatctgggt agcatatgct   7500
atcctaatct atatctgggt agtatatgct atcctaatct gtatccgggt agcatatgct   7560
atcctaatag agattagggt agtatatgct atcctaattt atatctgggt agcatatact   7620
acccaaatat ctggatagca tatgctatcc taatctatat ctgggtagca tatgctatcc   7680
taatctatat ctgggtagca taggctatcc taatctatat ctgggtagca tatgctatcc   7740
taatctatat ctgggtagta tatgctatcc taatttatat ctgggtagca taggctatcc   7800
taatctatat ctgggtagca tatgctatcc taatctatat ctgggtagta tatgctatcc   7860
taatctgtat ccgggtagca tatgctatcc tcatgcatat acagtcagca tatgataccc   7920
agtagtagag tgggagtgct atcctttgca tatgccgcca cctcccaagg gggcgtgaat   7980
tttcgctgct tgtccttttc cttataccgt cgacctctag ctagagcttg gcgtaatcat   8040
ggtcatagct gtttcctgtg tgaaattgtt atccgctcac aattccacac aacatacgag   8100
ccggaagcat aaagtgtaaa gcctggggtg cctaatgagt gagctaactc acattaattg   8160
cgttgcgctc actgcccgct ttccagtcgg gaaacctgtc gtgccagctg cattaatgaa   8220
tcggccaacg cgcggggaga ggcggtttgc gtattgggcg ctcttccgct tcctcgctca   8280
ctgactcgct gcgctcggtc gttcggctgc ggcgagcggt atcagctcac tcaaaggcgg   8340
taatacggtt atccacagaa tcaggggata acgcaggaaa gaacatgtga gcaaaaggcc   8400
agcaaaaggc caggaaccgt aaaaaggccg cgttgctggc gtttttccat aggctccgcc   8460
cccctgacga gcatcacaaa aatcgacgct caagtcagag gtggcgaaac ccgacaggac   8520
tataaagata ccaggcgttt ccccctggaa gctccctcgt gcgctctcct gttccgaccc   8580
tgccgcttac cggatacctg tccgcctttc tcccttcggg aagcgtggcg ctttctcata   8640
gctcacgctg taggtatctc agttcggtgt aggtcgttcg ctccaagctg gctgtgtgc    8700 acgaaccccc cgttcagccc gaccgctgcg ccttatccgg taactatcgt cttgagtcca   8760
acccggtaag acacgactta tcgccactgg cagcagccac tggtaacagg attagcagag   8820
cgaggtatgt aggcggtgct acagagttct tgaagtggtg gcctaactac ggctacacta   8880
gaagaacagt atttggtatc tgcgctctgc tgaagccagt taccttcgga aaaagagttg   8940
gtagctcttg atccggcaaa caaaccaccg ctggtagcgg tttttttgtt tgcaagcagc   9000
agattacgcg cagaaaaaaa ggatctcaag aagatccttt gatcttttct acggggtctg   9060
acgctcagtg gaacgaaaac tcacgttaag ggattttggt catgagatta tcaaaaagga   9120
tcttcaccta gatccttta aattaaaaat gaagttttaa atcaatctaa agtatatatg    9180
agtaaacttg gtctgacagt taccaatgct taatcagtga ggcacctatc tcagcgatct   9240
gtctatttcg ttcatccata gttgcctgac tccccgtcgt gtagataact acgatacggg   9300
agggcttacc atctggcccc agtgctgcaa tgataccgcg agacccacgc tcaccggctc   9360
cagatttatc agcaataaac cagccagccg gaagggccga gcgcagaagt ggtcctgcaa   9420
ctttatccgc ctccatccag tctattaatt gttgccggga agctagagta agtagttcgc   9480
cagttaatag tttgcgcaac gttgttgcca ttgctacagg catcgtggtg tcacgctcgt   9540
cgtttggtat ggcttcattc agctccggtt cccaacgatc aaggcgagtt acatgatccc   9600
```

```
ccatgttgtg caaaaaagcg gttagctcct tcggtcctcc gatcgttgtc agaagtaagt    9660
tggccgcagt gttatcactc atggttatgg cagcactgca taattctctt actgtcatgc    9720
catccgtaag atgcttttct gtgactggtg agtactcaac caagtcattc tgagaatagt    9780
gtatgcggcg accgagttgc tcttgcccgg cgtcaatacg ggataatacc gcgccacata    9840
gcagaacttt aaaagtgctc atcattggaa aacgttcttc ggggcgaaaa ctctcaagga    9900
tcttaccgct gttgagatcc agttcgatgt aacccactcg tgcacccaac tgatcttcag    9960 catctttttac tttcaccagc gtttctgggt gagcaaaaac aggaaggcaa aatgccgcaa   10020
aaaagggaat aagggcgaca cggaaatgtt gaatactcat actcttcctt tttcaatatt   10080
attgaagcat ttatcagggt tattgtctca tgagcggata catatttgaa tgtatttaga   10140
aaaataaaca aataggggtt ccgcgcacat ttccccgaaa agtgccacct gacgtc       10196
```